(12) United States Patent
Fan

(10) Patent No.: US 9,737,319 B2
(45) Date of Patent: Aug. 22, 2017

(54) ANTI-RETROPULSION SYSTEMS AND METHODS

(71) Applicant: GYRUS ACMI, INC., Southborough, MA (US)

(72) Inventor: Tailin Fan, Nashua, NH (US)

(73) Assignee: GYRUS ACMI, INC., Southborough, MA (US)

( * ) Notice: Subject to any disclaimer, the term of this patent is extended or adjusted under 35 U.S.C. 154(b) by 219 days.

(21) Appl. No.: 14/728,410

(22) Filed: Jun. 2, 2015

(65) Prior Publication Data

US 2015/0265300 A1 Sep. 24, 2015

Related U.S. Application Data

(62) Division of application No. 13/787,190, filed on Mar. 6, 2013, now Pat. No. 9,072,519.

(Continued)

(51) Int. Cl.
*A61B 17/221* (2006.01)
*A61B 17/12* (2006.01)
*A61B 17/22* (2006.01)

(52) U.S. Cl.
CPC ........ *A61B 17/221* (2013.01); *A61B 17/1204* (2013.01); *A61B 17/12031* (2013.01); *A61B 17/12099* (2013.01); *A61B 17/12145* (2013.01); *A61B 17/12168* (2013.01); *A61B 17/22* (2013.01); *A61B 2017/1205* (2013.01);
(Continued)

(58) Field of Classification Search
CPC ........ A61B 17/12022; A61B 17/12163; A61B 17/1204; A61B 17/12036; A61B 17/12031; A61B 17/12045; A61B 17/12109; A61B 17/12113; A61B 17/12122; A61B 17/1214; A61B 17/12145; A61B 17/12168; A61B 17/12172; A61B 17/12177; A61B 17/22031; A61B 2017/12127; A61B 17/320725; A61B 17/320733; A61F 2/01; A61F 2/013; A61F 2002/011; A61F 2002/015; A61F 2002/016; A61F 2002/018
See application file for complete search history.

(56) References Cited

U.S. PATENT DOCUMENTS 6,610,077 B1   8/2003   Hancock et al.
7,097,648 B1   8/2006   Globerman et al.
(Continued)

OTHER PUBLICATIONS

Rane, A et al., Making cases more predictable; Back Stop Stone Antirettopulsion Device, Urology, and women's health, Boston Scientific; pp. 1-6, Sep. 1, 2011.
(Continued)

*Primary Examiner* — Thomas McEvoy
(74) *Attorney, Agent, or Firm* — The Dobrusin Law Firm, P.C.

(57) ABSTRACT

An anti-retropulsion device comprising: an expandable segment; a distal collar positioned distally of the expandable segment; and a proximal collar positioned proximally of the expandable segment; wherein the expandable segment has a corresponding plurality of expandable members, and wherein each of the expandable members is configured to expand or contract radially and circumferentially in correspondence with a change in spacing between the distal collar and the proximal collar.

20 Claims, 13 Drawing Sheets

Related U.S. Application Data

(60) Provisional application No. 61/610,938, filed on Mar. 14, 2012.

(52) U.S. Cl.
CPC ............... *A61B 2017/2212* (2013.01); *A61B 2017/2217* (2013.01)

(56) References Cited

U.S. PATENT DOCUMENTS

| | | |
|---|---|---|
| 7,214,229 B2 | 5/2007 | Mitchell et al. |
| 7,462,183 B2 | 12/2008 | Behl et al. |
| 7,879,066 B2 | 2/2011 | Desai et al. |
| 7,883,516 B2 | 2/2011 | Huang et al. |
| 2005/0055034 A1* | 3/2005 | Bates ............... A61B 17/221 606/127 |
| 2005/0143827 A1 | 6/2005 | Globerman et al. |
| 2006/0229645 A1* | 10/2006 | Bonnette .......... A61B 17/00234 606/159 |
| 2008/0234722 A1* | 9/2008 | Bonnette ............... A61F 2/013 606/200 |
| 2010/0324538 A1 | 12/2010 | Van Orden |
| 2014/0214060 A1* | 7/2014 | Bonnette .......... A61B 17/32072 606/159 |

OTHER PUBLICATIONS

Urology, Cook Medical, Stone Entrapment and Extraction Device; Jan. 1, 2012 www.cookmedical/urology.com.

Paul K. Pietrow, MD University of Kansas Medical Center Kansas City, KS; Stone Cone Nitinol Retrieval Coil Technique, Boston Scientific Jun. 1, 2004.

* cited by examiner

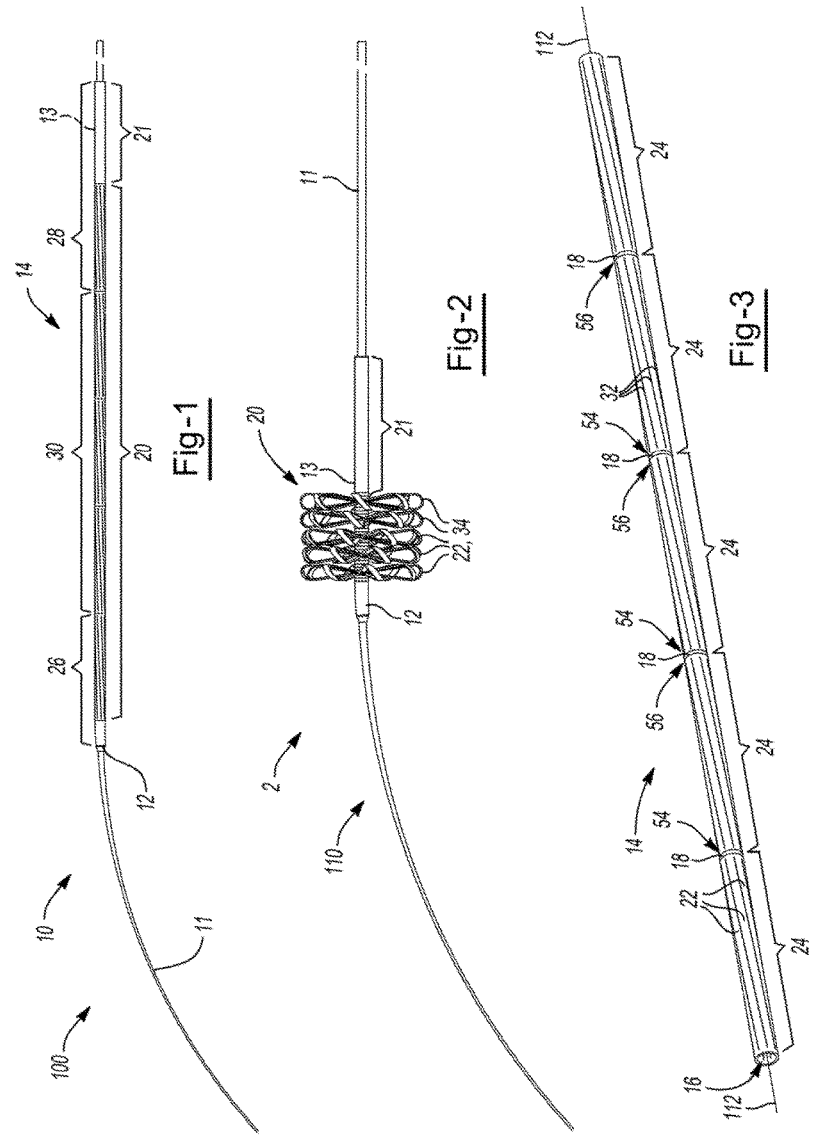

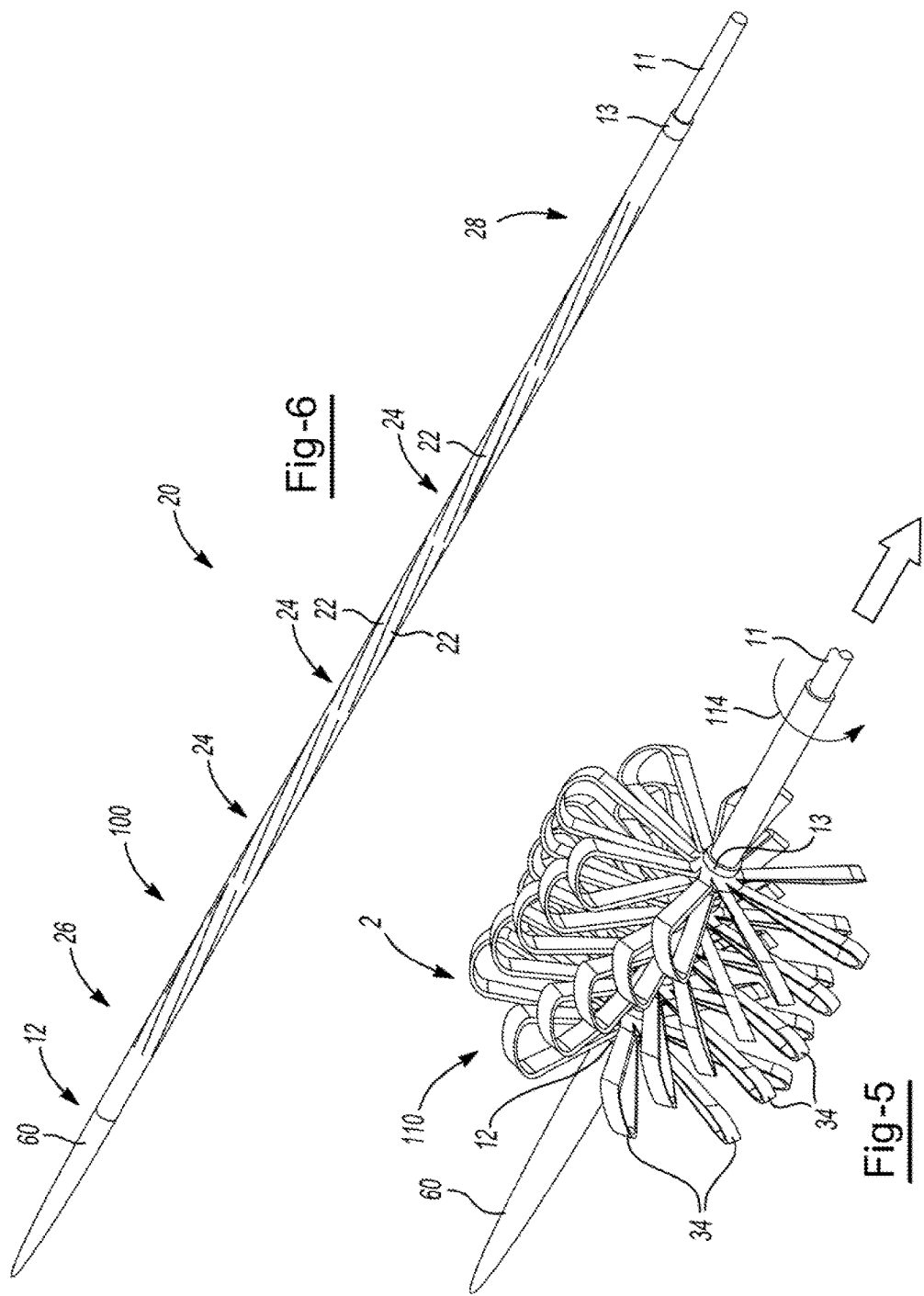

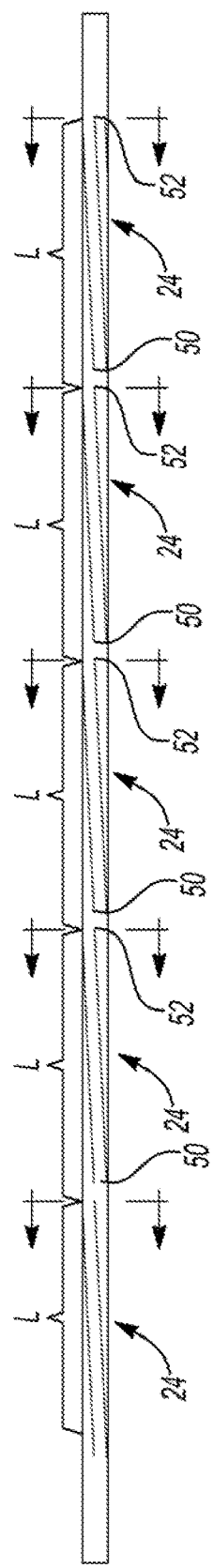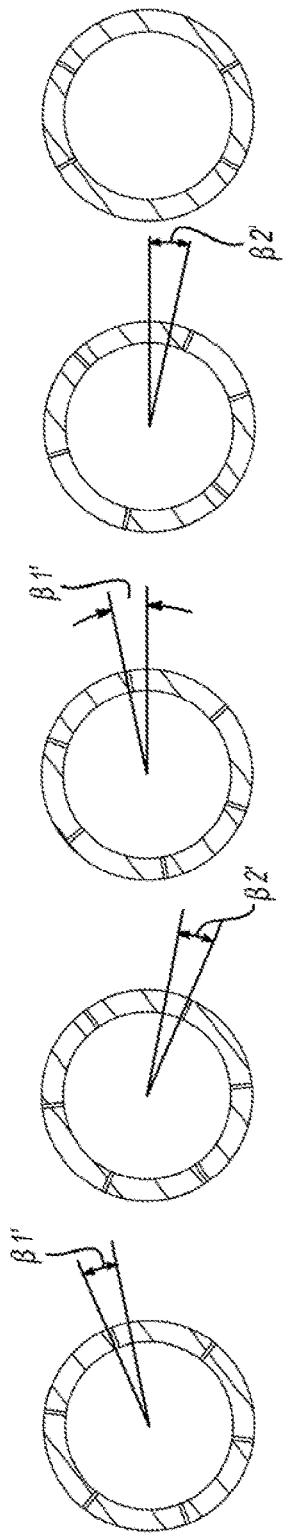
Fig-8

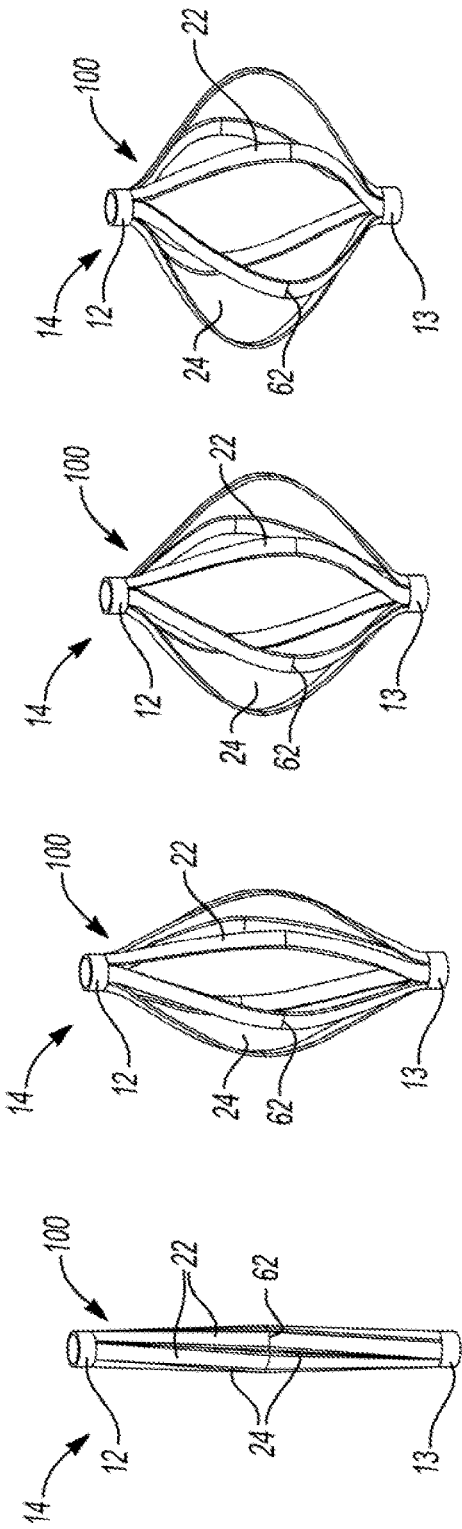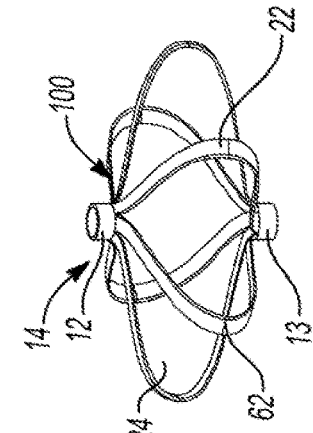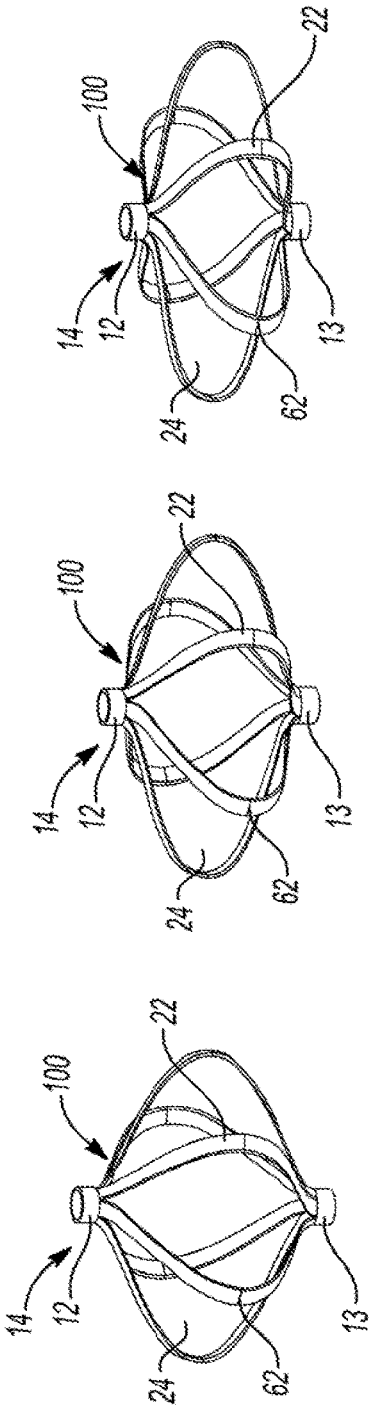

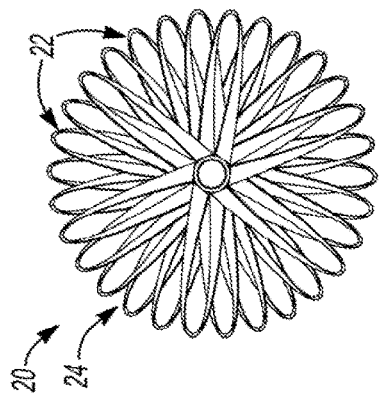
Fig-10A3
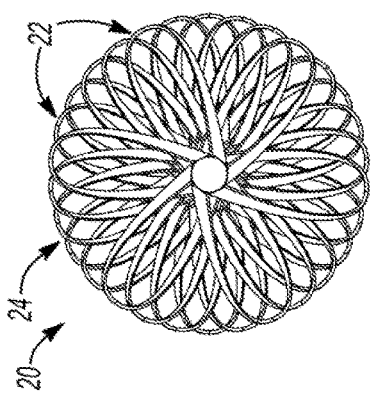
Fig-10B3
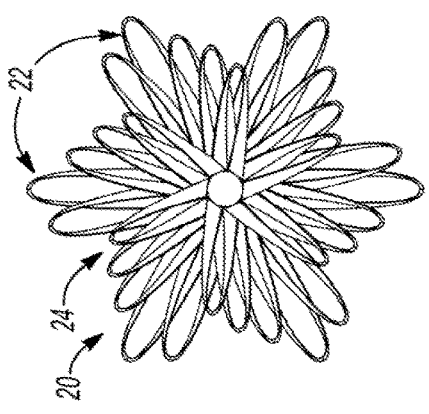
Fig-10A2
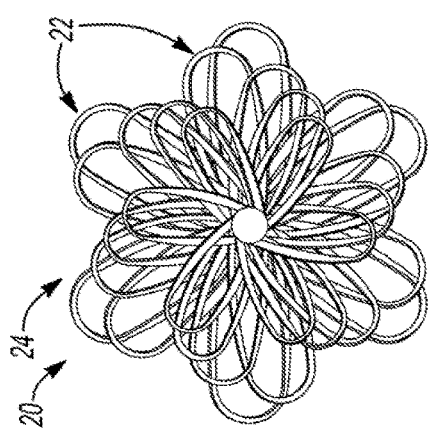
Fig-10B2
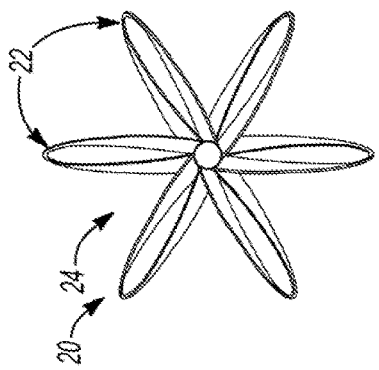
Fig-10A1
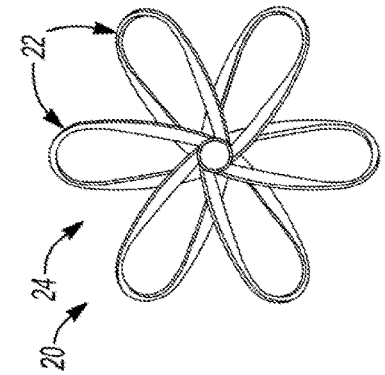
Fig-10B1

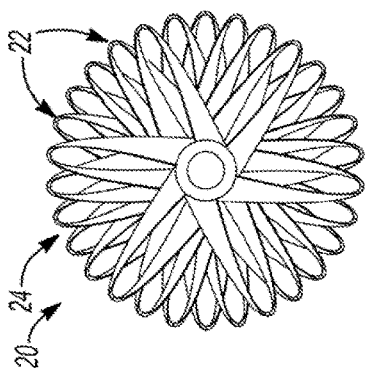
Fig-10C3
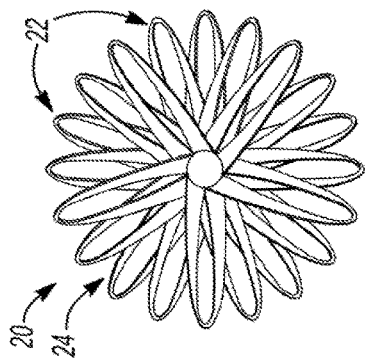
Fig-10D3
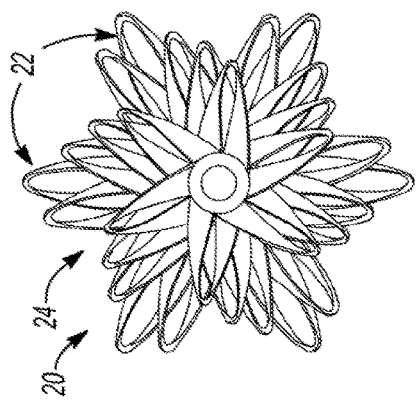
Fig-10C2
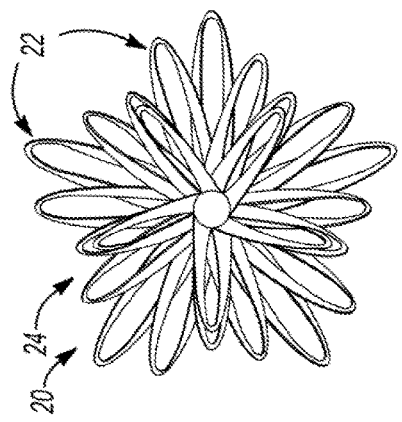
Fig-10D2
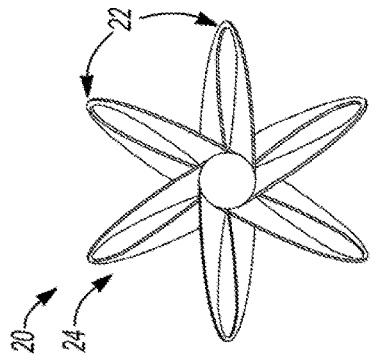
Fig-10C1
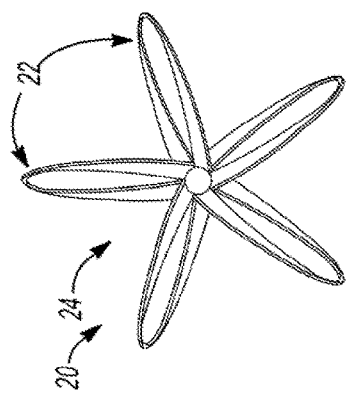
Fig-10D1

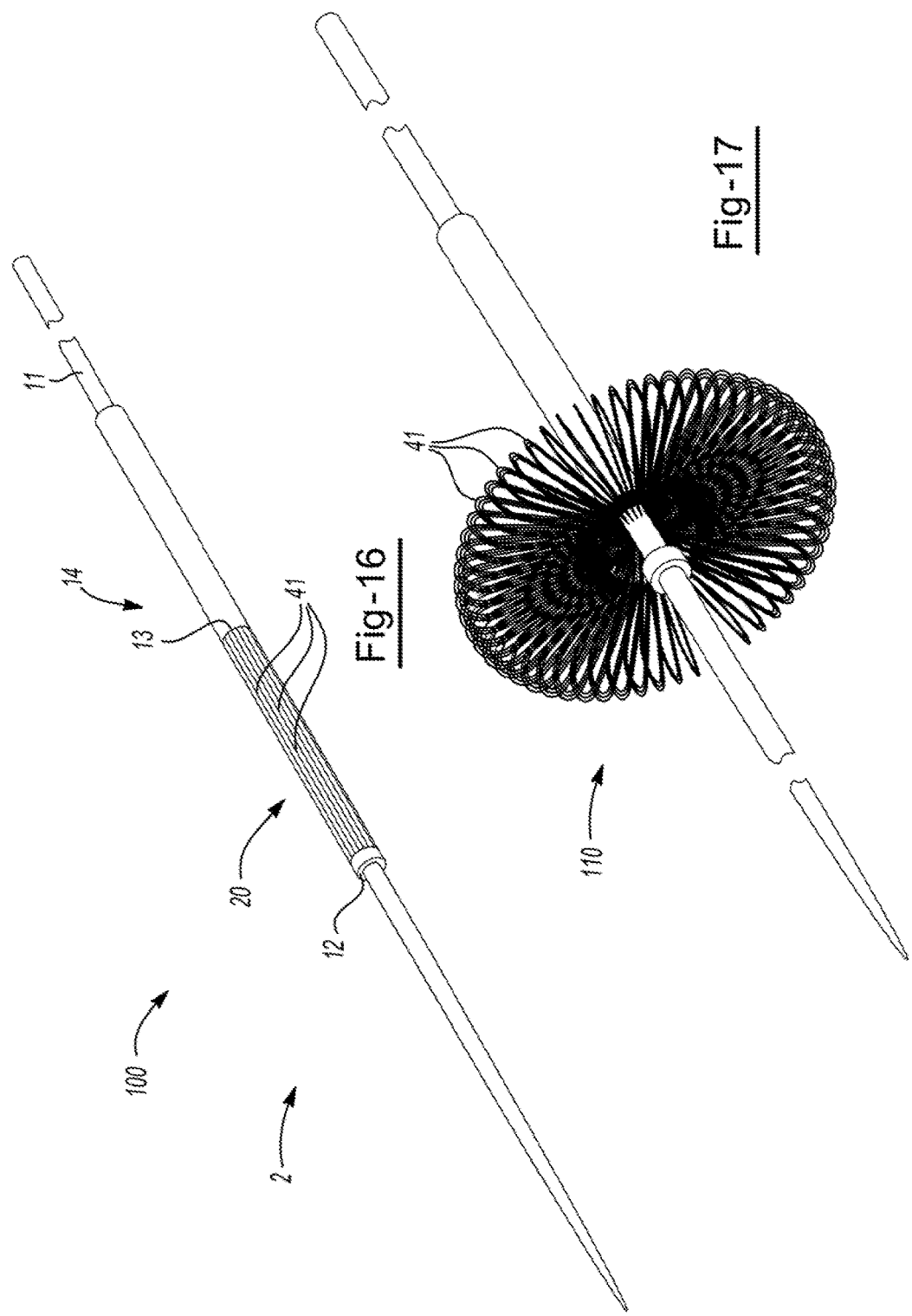

ANTI-RETROPULSION SYSTEMS AND METHODS

FIELD

The present teachings relate to a system for preventing retropulsion of a body and a method for deploying the system.

BACKGROUND

This application, and the innovations and related subject matter disclosed herein, (collectively referred to as the "disclosure") generally concern systems and methods related to reducing or eliminating retropulsion of a body or other debris within a body lumen during a surgical procedure. Such systems and methods are sometimes referred to as "anti-retropulsion" systems and methods. As but one example of systems and methods, of an innovative anti-retropulsion device can be configured and/or used to reversibly occlude a ureter during a urologic procedure to remove ureteral calculi ("kidney stones" that have dropped into the ureter from a corresponding kidney), e.g., during ureterolithotripsy. Current systems used to prevent anti-retropulsion may become damaged during a procedure and thus are not easily retracted or cease to prevent retropulsion of a body of debris. Some system once deployed from a 1-D state to a 3-D state cannot be compressed and easily retracted. Other systems have a generally 2D configuration and require additional steps to be performed to remove the system when the procedure is completed.

An example of a system is available from Boston Scientific and offers a Stone Cone™ Retrieval Coil. An example of another system is available from Cook. Medical and offers a NTrap® device. Another example of a system is available from Percsys and offers the Accordian® (see U.S. Pat. Nos. 7,462,183; 7,879,066; and 7,883,516 all of which are incorporated by reference herein for all purposes). Yet another example of a system is available from Boston Scientific and is sold under the name Backstop. Examples of some anti-retropulsion systems that may be used may be found in U.S. Pat. Nos. 6,610,077; 7,097,648; and 7,214,229 all of which are incorporated by reference herein for all purposes.

Despite prior proposals, anti-retropulsion devices have not been widely adopted by surgeons. Accordingly, there remains a need for effective, easy-to-use, and safe anti-retropulsion systems, apparatus, and methods. It would be attractive to have an anti-retropulsion system and method so that the anti-retropulsion system is extendable behind debris and can be retracted and removed from behind the debris. It would be attractive to have an anti-retropulsion system that is expandable to fill an entire cross-section of a body lumen. It would be attractive to have an anti-retropulsion system that can be used with a laser, a green laser, an ultrasonic device, or a combination thereof.

SUMMARY

The present teachings meet one or more of the present needs by providing: an anti-retropulsion device comprising: an expandable segment; a distal collar positioned distally of the expandable segment; a proximal collar positioned proximally of the expandable segment; wherein the expandable segment has a corresponding plurality of expandable members, wherein each of the expandable members is configured to expand or contract radially and circumferentially in correspondence with a change in spacing between the distal collar and the proximal collar.

The present teachings provide: an anti-retropulsion device comprising: an elongate tubular sleeve defining an outer wall having: a proximal wall portion defining a first plurality of apertures, each of the first plurality of apertures having: a proximal end, and a distal end; a distal wall portion longitudinally spaced from the proximal wall portion, the distal wall portion defining a second plurality of apertures having: a proximal end, and a distal end; and an intermediate wall portion located between the proximal wall portion and the distal wall portion; wherein the proximal end and the distal end of each of the first plurality of apertures, the second plurality of apertures, or both are positionally offset in an ordinate direction, wherein each of the proximal ends of the second plurality of apertures are offset in an ordinate direction from each of the distal ends of the first plurality of apertures; and an apparatus configured to urge a distal end of the elongate tubular sleeve toward a proximal end of the elongate tubular sleeve.

The present teachings provide: a method comprising: positioning an anti-retropulsion device at a desired location and moving a core wire so that a distance between a distal collar and a proximal collar is reduced and an expandable portion is expanded.

The present teachings provide an anti-retropulsion system and method so that the anti-retropulsion system is extendable behind debris and can be retracted and removed from behind the debris. The present teachings provide an anti-retropulsion system that is expandable to fill an entire cross-section of a body lumen. The present teachings provide an anti-retropulsion system that can be used with a laser, a green laser, an ultrasonic device, or a combination thereof.

BRIEF DESCRIPTION OF THE DRAWINGS

The innovations disclosed herein overcome many problems in the prior art. Unless specified otherwise, the accompanying drawings illustrate aspects of the innovative subject matter described herein.

FIG. 1 illustrates a side-elevation view of an anti-retropulsion device ("ARD") operably coupled with guidewire in an insertion configuration.

FIG. 2 illustrates a side-elevation view of the ARD shown in FIG. 1 in a deployed state as after insertion from a lumen.

FIG. 3 illustrates a magnified isometric view from alongside a sheath of the ARD shown in FIG. 1, in an insertion state.

FIG. 4A shows an isometric view of the ARD and FIG. 4B shows an end-elevation view of the ARD.

FIG. 5 illustrates an isometric view of another ARD in a transformation to a deployed state.

FIG. 6 illustrates an isometric view of the ARD shown in FIG. 5 in an insertion state.

FIG. 8 illustrates several details of another embodiment of a sheath of an ARD.

FIG. 9A-9K illustrates a sequence of isometric views of an expandable segment of an ARD as disclosed herein. The sequence of views shows several intermediate configurations of the expandable segment as it radially expands and axially contracts from an insertion state to a deployed state.

FIG. 10A1-10D3 illustrates several alternative configurations of radially expanded ARDs.

FIG. 16 illustrates an alternative embodiment of an ARD, in an insertion state, with an expandable segment having several fiber strands forming the corresponding expandable members.

FIG. 17 illustrates the ARD shown in FIG. 16 positioned in a deployed state.

DETAILED DESCRIPTION

Figure 4A:
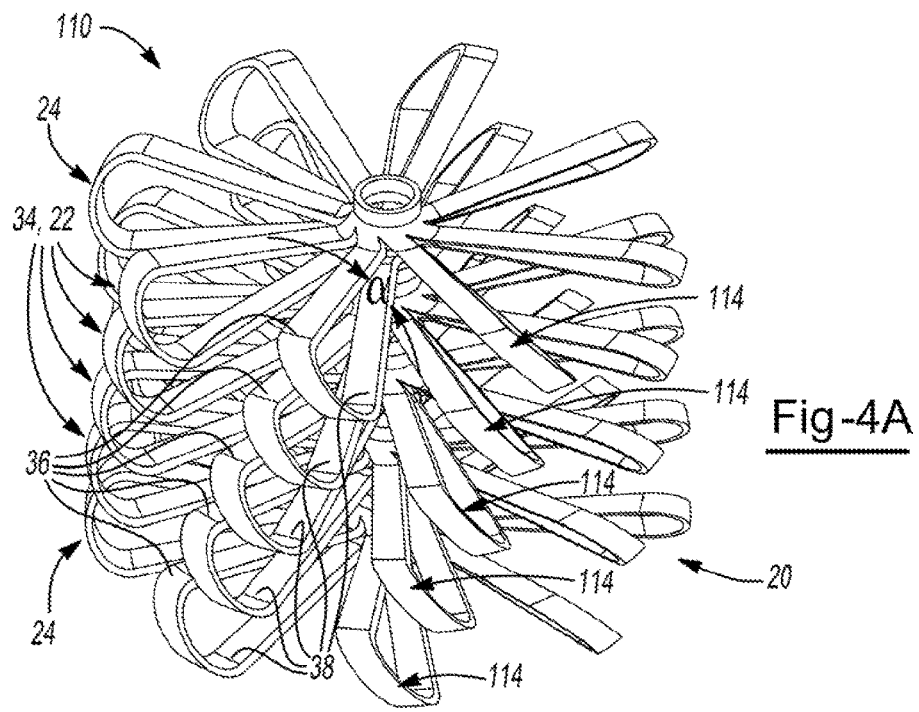
FIGS. 4A and 4B illustrate an example of a radially expanded and longitudinally contracted ARD in a "deployed state".

The features and advantages of disclosed systems and methods will become more apparent from the following detailed description, which proceeds with reference to the accompanying drawings, wherein like numerals refer to like features throughout the drawings and this specification. The following describes various principles related to reducing or eliminating retropulsion of a foreign body or other debris within a body lumen during a surgical procedure. Systems, apparatus and methods described in relation to any particular applications, configurations, or uses, are mere examples incorporating one or more innovative principles disclosed herein, and are used to illustrate one or more aspects of the innovative principles. Accordingly, systems, apparatus, and methods different from those shown and described herein can embody such innovative principles, or can be used in applications not described herein in detail. Accordingly, such alternative embodiments also fall within the scope of this disclosure. Mechanical anti-retropulsion devices (ARDs) can geometrically transform from an insertion state, or configuration, to a deployed state, or configuration. In an insertion state, a mechanical ARD may have a dimension small enough, at least measured along one coordinate direction, to pass through a gap positioned between a body of debris within a lumen (e.g., ureteral calculi, or a "stone") and a nearby wall of the lumen (e.g., a ureter). After being positioned, at a desired position, distally of the body of debris, the mechanical ARD may be activated (e.g., expanded, unfurled) to transform its geometry from the insertion state to a deployed state, in which the mechanical ARD has sufficiently large dimensions transverse to the lumen (e.g., measured along at least two coordinate directions) to at least partially occlude the lumen (e.g., to obstruct, or prevent the passage of, a stone from retrograde movement beyond the ARD, as during lithotripsy). Such an obstruction may block a ureter, and prevent a stone from moving in a retrograde direction past the radially expanded device.

Geometric transformation of mechanical ARDs may be summarized (or classified) according to their respective geometric abstractions, as follows:

One-dimensional ("1-D"): if an elongate structure is sufficiently slim (e.g., has a sufficiently large dimension along one coordinate direction relative to the other two coordinate directions) in comparison with a characteristic dimension of a lumen (e.g., a diameter of a ureter), such as, for example, a guidewire, the structure can be considered as having a 1-D geometry in the abstract, with a "long" dimension extending along a longitudinal axis of the guidewire;

Two-dimensional ("2-D"): if a structure has two dimensions along two coordinate directions, respectively, that are substantially larger than a third dimension along the respective third coordinate dimension, such as a thin membrane, the structure can be considered as having a 2-D geometry in the abstract. (A structure having a 2-D configuration, if placed across (e.g., transversely relative to) a lumen can obstruct the lumen similarly to a diaphragm).

Some apparatus disclosed herein may transform a respective configuration from an insertion state to a deployed state. In the deployed state, the apparatus can be relatively less prone to damage (e.g., as from laser energy) compared to conventional ARDs. As well, the ARDs of the teachings herein may be relatively safe and have an acceptably low cost.

In addition to general requirements for devices of in-patient usage, such as biocompatibility, disclosed systems and methods can have one or more of the following characteristics:

(1) Reliable, able to keep the debris (e.g., stone) in place, to localize the debris, or to limit the extent of retropulsion during the procedure;
(2) Radio-opaque for tracking;
(3) Resistant to damage from a laser or other energy source, e.g., a mechanical lithotripter;
(4) Relatively safe for patient even, e.g., even when directly illuminated by Ho:YAG laser beam;
(5) Readily deployable, reversible, and removable (e.g., quick retrieval of such a device from the ureter is possible), at any time during a procedure (e.g., lithotripsy);
(6) In certain embodiments, prior to insertion, the device typically has an outer-diameter ("OD") similar to a guidewire OD (e.g., about 1.0 mm (3 Fr));
(7) In certain embodiments, after insertion, able to span a lumen as large as about 10.0 mm (30 Fr) inner-diameter ("ID");
(8) self-adjustable to lumen size;
(9) In addition to reducing or eliminating retropulsion of an debris, some disclosed apparatus can be used to retrieve (e.g., remove) all or part of the debris, or otherwise manipulate a target;
(10) During retrieval, able to automatically detent for the purpose of, e.g., avoiding over stressing the corresponding lumen (e.g., ureter) in narrow passages; and
(11) Relatively low cost and/or disposable.

A mechanical ARD in an insertion state may have an elongate ("1D" or "generally linear") or a substantially planar ("2D") configuration. In either instance, the ARD may be substantially thin in an insertion configuration, allowing the ARD to bypass a stone to reach a space behind it, while not pushing the stone in a retrograde direction along the lumen. For example, before being transformed into a configuration that occupies a substantial space, or volume, (e.g., to form a "plug" to block a stone's retrograde path), the ARD may have a relatively small 3-D configuration (e.g., a "dot"), a thin, elongate configuration (e.g., a "wire"), or a thin, substantially planar structure (e.g., a furled "banner"). As for material, an ARD may be made of a metal, a polymer, or both in the form of tube, mesh, fiber, or a combination thereof, or other materials discussed herein. The expandable portion can be a tube of a selected material, (e.g., metal, plastic, or polymer film, or a bundle of natural or synthetic fiber wrapped around into a tubular shape).

As used herein, the term "insertion configuration" or "insertion state" means a configuration suitable for inserting (or removing) an anti-retropulsion device in a body lumen. As used herein, the term "deployed configuration" or "deployed state" means a configuration suitable for performing an intended occultation localization function within a body lumen. In a deployed state, the distal collar and the proximal collar may be urged apart from each other. In one example, the distal collar may be fixedly coupled to the distal end of the expandable portion of the ARD and the proximal collar may be fixedly coupled to the proximal end of the expandable portion, allowing the expandable portion to longitudinally expand and radially contract as the spacing of the distal collars and the proximal collars changes relative to each other so that the ARD is changed from an insertion configuration to a deployed configuration.

The ARD of the teachings herein may have any configuration so that the ARD may be placed behind a body of debris and expanded upon achieving a desired location behind the body of debris. The ARD when in the insertion configuration may have a largest dimension in a longitudinal direction (e.g., along a longitudinal axis or length). The ARD in an insertion configuration may generally be 1D (e.g., have a length in the z-direction and be substantially flat in x- and y-directions). The ARD when in the insertion configuration may have a largest dimension (other than a length) that is sufficiently small so that the ARD may fit through a gap. For example, the largest dimension may be a cross-sectional length. The largest dimension of the ARD (other than the length) in the insertion configuration may be substantially constant along the length and/or longitudinal axis. The, largest dimension may vary along the longitudinal axis of the ARD, the length or the ARD, or both. The largest dimension (other than a length) in the insertion configuration may be about 0.2 mm or more, about 0.5 mm or more, or about 1.0 mm or more. The largest dimension (other than a length) in the insertion configuration may be about 5 mm or less, preferably about 3 mm or less, or more preferably about 2 mm or less. Preferably, the largest dimension is a dimension from about 0.7 mm or about 1.3 mm and more preferably from about 0.8 mm to about 1.2 mm.

The ARD may have a largest dimension (other than length) (e.g., a cross-sectional length) in the deployed configuration that is sufficiently large that the lumen is completely filled; the body of debris is immobilized from retrograde movement; the lumen is not damaged, or a combination thereof. In a deployed state, the expanded portion of the ARD may occupy a three-dimensional ("3-D") volume (e.g., expanded radially and circumferentially in response to a longitudinal contraction) that is large enough to prevent debris from moving in a retrograde direction (or minimize the extent to which the debris can move in the retrograde direction). For example, the ARD may prevent movement of debris as forces are applied to the debris during a removal procedure. In some embodiments, the occultation may be sufficient to allow the expanded portion of the device to collect the stone (or debris) fragments and/or to facilitate their eventual removal from the operation site so that the ARD can be used as a "stone basket" to remove debris from the operation site. A geometric transformation from an insertion state to a deployed state may be reversible, promoting relative patient safety by allowing the device to be removed during or after a surgical procedure.

The ARD may have a largest dimension (other than length) in the deployed configuration that is about 3 mm or more, preferably about 5 mm or more, more preferably about 8 mm or more, or even more preferably about 10 mm or more. The ARD may have a largest dimension (other than length) in the deployed configuration that is about 20 mm or less, about 15 mm or less, or about 12 mm or less. The largest dimension (e.g., cross-sectional length) may be from about 7 mm to about 13 mm, preferably from about 8 mm to about 12 mm, and more preferably from about 9 mm to about 11 mm. The ARD may have a largest dimension (other than length) in the deployed configuration that varies along the length of the ARD. For example, the ARD may have a largest dimension of about 10 mm on a distal end and a largest dimension of about 8 mm on a proximal end, or vice versa. The ARD may be comprised of one or more expandable segments and each expandable segment may have a different largest dimension when in the deployed configuration. For example, the ARD may have five expandable segments and the largest segment may be about 10 mm and the smallest segment may be about 7 mm and the length of the segments may taper between the first segment and fifth segment. In another example, the third segment may be the largest segment and may have a length of about 10 mm and the first and fifth segments may have a length of about 8 mm and the second and fourth segments may have a length of about 9 mm. The largest dimension of the ARD (other than length) may be variable so that the ARD varies to match the size of the lumen. The largest dimension of the ARD (other than length) in the insertion configuration and the deployed configuration may be a cross-sectional length (e.g., diameter). The ARD may include one or more insertion cones, one or more sheaths; one or more core wires; one or more collars (e.g., distal collar, intermediate collar, proximal collar, or a combination thereof); or a combination thereof.

The one or more insertion cones may be any structure that has a generally tapered shape that assists an ARD in fitting through a gap between a wall of a body lumen and debris in the body lumen. The one or more insertion cones may have a point and taper to the same size as the sheath in the insertion configuration. The one or more insertion cones may include a through hole so that one or more devices may pass through the insertion cone, the ARD, or both. For example, a core wire, a guidewire, or both may pass through the insertion cone, the ARD, or both. The one or more insertion cones may have a conical shape, a tapered shape, a blunt tip, a rounded tip, an angled tip, flat tip, or a combination thereof so that the insertion cone assists in guiding the ARD through a gap. The insertion cone may include a collar, may be a collar, may assist in locking a collar to a sheath, or a combination thereof. The insertion cone may cover an insertion end of a sheath so that the insertion end of the ARD is smooth and may be free of an edge to catch and prevent insertion movement. The insertion cone may be a discrete piece, may be part of the sheath, may be interconnected with the sheath and the core wire, or a combination thereof.

The one or more sheaths have both an insertion configuration and a deployed configuration. The one or more sheaths in the insertion configuration may have a dimension that is sufficiently small so that the one or more sheaths fit through a gap between a piece of debris and a lumen wall. The one or more sheaths may be an elongate tubular sleeve. Before transforming from an insertion configuration to a deployed configuration, an innovative ARD may have a generally "tubular" (e.g., annular, cylindrical) elongate shape. Although described as "generally tubular", such elongate structures may have slits, holes, or both extending partially or wholly through a portion of the sheath (e.g., an annular wall) Other cross-sectional shapes apart from round or annular cross-sections are possible. Examples of a generally tubular, elongate structure is a goose neck spiral, a wire woven jacket, a geometry cut from a tube or laid out by individual filaments, the like, or a combination thereof. An outer diameter of a generally tubular, elongate device, in an insertion state, can be about the same as a sheath used to deliver the device to a surgical site (e.g., about 1 mm). The device may have a substantial length, providing a relatively high dimensional aspect ratio. Such an elongate device may be characterized as having a 1-D configuration in the insertion state. The one or more sheaths may have an outer wall, a hollow interior region, one or more expandable portions, one or more non-expandable portions, or a combination thereof.

The sheath may include one or more expandable portions, one or more non-expandable portions, or both. Preferably, the sheath includes a non-expandable portion on each terminal end and two or more expandable portions therebetween. The sheath may be free of non-expandable portions. The expandable portions, the non-expandable portions, or both may include a hollow interior region.

The hollow interior region may extend axially through the longitudinal axis of the sheath. The hollow interior region may taper along the longitudinal axis of the sheath. The hollow interior region may be separated by internal dividing walls. For example, the one or more sheaths may be divided into three discrete hollow interior regions by two internal dividing walls that reduce a size of an opening in the sheath. The outer wall of the one or more sheaths in the insertion configuration may have a generally circular cross-section, an oval cross-section, a diamond cross-section, a malleable cross-section, or a combination thereof so that the one or more sheaths fit through a gap. The one or more sheaths have a distal end region, a proximal end region, and an intermediate region between the distal end region and the proximal end region. The one or more sheaths may be made of any biocompatible material. The one or more sheaths may be comprised of a plurality of fibers made from a material discussed herein. The fiber may be combined together in a manner so that upon contraction of a collar the fibrous sheath expands. The one or more sheaths may be made of a material with sufficient rigidity that the material may be inserted by being pushed or pulled. The one or more sheaths may be made of a material with sufficient elasticity so that the material bends, folds, deforms, buckles, or a combination thereof when a force is applied. The one or more sheaths may be made of a material with sufficient flexibility so that when all or a portion of the sheaths contacts a wall of a lumen the sheath deforms so that the lumen is not damaged, injured, or both. The one or more sheaths may be made of a natural material, a synthetic material, a metal, a polymer, an elastomer, polyethylene, polyethylene terephthalate, a polyamide, or a combination thereof. The expandable portions of the one or more sheaths may include one or more slits, apertures, cuts, or a combination thereof (hereinafter referred to as "slits") and preferably a plurality of cuts, apertures, slits, or a combination thereof.

The one or more slits may be located at any location along the longitudinal axis, an outside (e.g., circumference), or both of the sheath. The one or more slits may be located in the distal end region, the proximal end region, the intermediate end region, or a combination thereof. The one or more slits may be grouped together around an outside, at a region along the longitudinal axis, or both of the sheaths. Preferably, at least one group of slits is located in each region. More preferably, the proximal end region includes one group, the distal end region includes one group, and the intermediate region includes three groups of slits.

Each group of slits may include one or more slits. Preferably, each group of slits is a plurality of slits that are circumferentially spaced apart around an outside of the sheath. Each group of slits may include one or more, two or more, three or more, four or more, preferably five or more, or even more preferably six or more slits. The number of slits may be directly proportional to the number of expandable members in each expandable segment. The number of slits may be inversely proportional to the width of each expandable member. For example, a segment including 3 slits will have an average slit width of about 120 degrees, whereas a segment including 6 slits will have an average slit width of about 60 degrees.

The "slit" (or aperture, sometimes referred to as a "cut") may be oriented at an oblique angle relative to the tube's longitudinal axis (e.g., forms a portion of a helix). Depending on the material that composes the tubular structure, the oblique angle may help the expandable components cover, or extend across, the lumen's cross-section in a deployed state. For example, the plurality of longitudinally spaced segments can correspond to an expanded configuration suitable for reversing the transformation (e.g., for collapsing from an expanded, deployed state back to an extended, insertion state). For example, longitudinally separated, expanded members otherwise might become entangled with each other and be hard to untangle when attempting to remove the ARD. Respective expandable members corresponding to longitudinally adjacent segments of an ARD may be circumferentially offset from each other. For example, each respective longitudinally adjacent segment can define a corresponding plurality of longitudinally extending apertures (or slits), defining a corresponding plurality of expandable members having a respective proximal end and a respective distal end. The oblique angle of the slits may be a circumferential angle between a proximal end and a distal end of each slit that may be as much as about 180. For example, a suitable offset angle may be between about 30 degrees and about 90 degrees, or between about 50 degrees and about 70 degrees. In some embodiments, a circumferential angle between a proximal end and a distal end of a selected slit can be about 60 degrees. The circumferential angle between a proximal end and a distal end of a slit may be about 5 degrees or more, about 8 degrees or more, about 10 degrees or more, about 12 degrees or more, or even about 15 degrees or more. The circumferential angle may be about 90 degrees or less, about 75 degrees or less, about 60 degrees or less, about 45 degrees or less, or about 30 degrees or less. For example, a proximal end of a slit begins at a 0 degree location and the sheath is rotated about 60 degrees to the distal end so that the slit has a circumferential angle of about 60 degrees. Each segment of the sheath may include one or more slits around the outside of the slit and each of the slits may have a different circumferential angle. Preferably, each of the slits has the same circumferential angle.

The expandable members corresponding to each of the segments may be offset in a circumferential direction from the expandable members corresponding to a respective adjacent longitudinally spaced segment. By circumferentially offsetting longitudinally adjacent expandable members, the respective "petals" formed from expanded members can be circumferentially offset from each other, substantially filling a cylindrical or conical volume and preventing the formation of longitudinally extending gaps between circumferentially adjacent 'petals'. A substantially filled cylindrical or conical volume may block a body lumen and prevent debris from moving past the volume. Longitudinally adjacent segments may be circumferentially offset from each other by a selected angle. An angle of circumferential offset between respective adjacent proximal ends of longitudinally adjacent slits, $A_s$, can be calculated from $A_s=360/(S*N)$, where S is the number of expandable members in a given segment, and N is the number of segments. For example, in a component having 5 segments, with each segment defining 6 expandable members, a circumferential offset between respective proximal ends of longitudinally adjacent expandable members will be about 12 degrees. The circumferential offset may be about 5 degrees or more, about 8 degrees or more, about 10 degrees or more, about 12 degrees or more, or about 15 degrees or more. The circumferential offset may be about 30 degrees or less, about 25 degrees or less, or about 20 degrees or less. The amount of circumferential offset may be dependent upon the number of expandable members in each segment.

Twisting the ARD, the sheath, or both during deployment can introduce such an angle between adjacent, radially expanded members, and can vary the cross-section coverage achieved by the expanded component (i.e., a twist angle). The twist angle may be any angle that assists in sufficiently filling an inner volume of a body lumen. The twist angle may be sufficiently large so that the deployed expandable members (i.e., petals) fill the inner volume of a body lumen and the body lumen is free of any longitudinally extending gaps between circumferentially adjacent petals. The twist angle may be sufficiently large so that each expandable member has an upper portion and a lower portion that are separated, but the not so large of a twist angle so that an inner diameter of the sheath is decreased in the deployed configuration. The twist angle may be about 5 degrees or more, about 8 degrees or more, about 10 degrees or more, about 12 degrees or more, or about 15 degrees or more. The twist angle may be about 90 degrees or less, about 60 degrees or less, about 45 degrees or less, about 30 or less, about 25 or less, or about 20 degrees or less. The amount of twist may be limited by a torsional limiter.

A torsional limiter may be any device that may limit the angle that the sheath may be twisted in an insertion configuration, a deployed configuration, or any configuration therebetween. A torsional limiter may be a portion of the distal collar, the proximal collar, or both. A torsional limiter may be one or more cuts, one or more absences of material, one or more notches, or a combination thereof in a sheath that a portion of, a projection from, or both of a core wire, a proximal collar, a distal collar, or both extend from and into the sheath, or vice versa so that the sheath, the core wire, the distal collar, the proximal collar, or a combination thereof may only be rotated a predetermined distance. The torsional limiter may be used to lock the twist angle once a predetermined twist angle is achieved. For example, the core wire, the distal collar, the proximal collar, the sheath, or a combination thereof may be twisted to one of the one or more notches, the one or more cuts, the one or more absences of material, or a combination thereof and locked within, held in place by, or both a friction fit, a mechanical interlock, or both by a portion of the core wire, the proximal collar, the distal collar, the sheath, or a combination thereof connecting an adjacent component. The amount of twist may be dependent upon the number of expandable members in each segment.

A number of expandable members between circumferentially spaced apertures, or slits, in a deployed state can be increased by increasing the number of longitudinally spaced segments, particularly if longitudinally adjacent expandable members are angularly offset from each other in a circumferential direction. With relatively more expandable members available by having a plurality of longitudinally spaced segments, damage to a few strands (e.g., damage that can occur during a surgical procedure) may have less impact on the blocking capacity of the expanded component as compared to an embodiment having relative fewer strands. A sheath may have one or more expandable segments along a longitudinal axis of the sheath. Preferably, the sheath has a plurality of expandable segments along a longitudinal axis of the sheath. The sheath may have 1 or more, 2 or more, preferably 3 or more, more preferably 4 or more, or even more preferably about 5 or more expandable segments along a longitudinal axis of the sheath. The sheath may even have 6, 7, 8, 9, or 10 expandable segments. Each expandable segment may include a group of expandable members.

Each group of slits may have a length and thus each group of expandable members (i.e., petals in the deployed state) may have substantially the same length. Preferably the length of each group of slits and each group of expandable members is substantially the same More preferably, each group of slits around the outside of the sheath has the same length in the insertion configuration and the deployed configuration. The length of each group of slits may vary depending on the desired cross-sectional distance of a lumen (e.g., diameter). The length of each group of slits may vary from segment to segment. For example, if the lumen is 10 mm in cross-sectional length then at least one of the groups of petals corresponding to the slits may have a length in the insertion configuration of about 10 mm. Thus, for example, upon buckling the petals corresponding to the slits may extend about 5 mm from each side so that the deployed cross-sectional length of the sheath is about 10 mm. In another example one group of petals corresponding to slits in one segment may have a length of 10 mm and another group of slits in another segment may have a length of about 9 mm. The expandable members may have a ratio of an insertion configuration longitudinal length to a deployed configuration cross-sectional length. The ratio may be any ratio so that in the insertion configuration the ARD may pass by debris in a lumen and so that when deployed the ARD prevents the debris from being moved retrograde in a lumen. The ratio of insertion configuration longitudinal length to deployed configuration cross-sectional length may be about 1:2 or more, about 1:5 or more, about 1:7 or more, preferably about 1:8 or more, more preferably about 1:9 or more, or most preferably about 1:10 or more. The ratio of insertion configuration cross-sectional length to deployed configuration cross-sectional length (e.g., ratio of expansion) may be about 1:20 or less, about 1:15 or less, or about 1:12 or less. However, one segment may have a ratio from about 1:8 to about 1:9 and another ratio may have a ratio from about 1:9 to about 1:10. The longer the length of each of the groups of expandable members in the insertion configuration may make the expandable members more susceptible to buckling. However, each of the expandable members may include one or more buckling features.

The expandable members may include one or more buckling features. The one or more buckling features may be any feature that weakens all or a portion of the expandable members so that the expandable members buckle at the buckling feature forming petals. The buckling feature may be an absence of material so that the structural integrity of the expandable member is lower at the buckling feature. The buckling feature may be an additional feature or device that is added to an expandable member so that the expandable member buckles, folds, bends, or a combination thereof at a predetermined location. Preferably, the buckling feature is a weakening of the one or more expandable members so that the expandable members bend, fold, or buckle at a predetermined location. The buckling features may be created by adding a hole, removing material from a thickness of the expandable members, removing material from a width of the expandable members, scoring all or a portion of the expandable member, including a window in a portion of the expandable member, cutting the expandable members and connecting back together with another material, or a combination thereof. The one or more buckling features may be oriented so that the expandable segments buckle in a specific order. For example, the bucking features may have more material removed in the groups of expandable members located near the proximate end region, the distal end region, the intermediate region, or a combination thereof. The length of the expandable members may dictate the buckling order of the expandable members. For example, the longest expandable members may buckle first. The width of the expandable members may dictate the buckling order. For example, the thinnest expandable members may buckle first. The buckling sequence may be determined by length, width, thickness, number of buckling features, location of the buckling features, or a combination thereof.

The sheath may be supported by and/or substantially wrapped around one or more adjoining structures that assist in insertion, deployment, retraction, or a combination thereof. The sheath may have one or more core wires that extend through a hollow interior region of the sheath. The one or more core wires may be any device that provides support to the sheath; assists in inserting the sheath; assists in deployment of the anti-retropulsion device; assists in retraction of the sheath assists in rotation of the sheath and/or one or more expandable members; or a combination thereof. The one or more core wires may be any material that is rigid or has a longitudinal strength so that the core wire may be used to move a sheath along its longitudinal axis. The one or more core wires may be a braided material. The one or more core wires may be two or more longitudinal wires that are substantially parallel along their respective longitudinal axes. The one or more core wires may be made of any material that is biocompatible. The one or more core wires may be made of a natural material, a synthetic material, a polymer; a plastic, a metal, nylon, stainless steel, or a combination thereof. The one or more core wires may be a guidewire that is found in an endoscope and the sheath may fit over the guidewire so that the sheath may be moved to a predetermined position. The one or more core wires may be connected to the sheath by one or more collars.

The one or more collars may be located at any location on the sheath, the one or more core wires, or both so that the one or more collars assist in holding the sheath on the one or more core wires, deploying the ARD, inserting the ARD, contracting the ARD, rotating all or a portion of the sheath, or a combination thereof. The one or more collars may be fixed relative to the insertion cone, the sheath, the core wire, or a combination thereof. The one or more collars may be movable relative to the sheath, the guidewire, the insertion cone or a combination thereof. Preferably, at least one collar is fixed relative to both the sheath and the core wire and at least one collar is moveable relative to the core wire. For example, a collar on one end may be fixed and when the core wire is pulled in a direction opposite to the insertion direction, the movable collar may move along the longitudinal axis of the core wire towards the fixed collar, or vice versa so that the expandable members are expanded. One or more collars may be located in a distal end region (i.e., distal to the user), a proximal end region (i.e., proximal to the user), an intermediate region (i.e., between the distal end region and the proximal end region), or a combination thereof. Preferably, at least one collar is located in a distal end region (i.e., distal collar) and at least one collar is located in the proximal end region (i.e., proximal collar). The one or more collars may be any device that is biocompatible and assist in holding the sheath, the core wire, or both. The one or more collars may be crimped, connected, folded, snapped, glued, welded, mechanically interlocked, or a combination thereof to form a fixed connection. The one or more movable collars may be the non-expandable portion of the sheath. For example, the portion of the sheath that is free of slits may form the movable collars. The one or more movable collars may bond one or more fiber strands, one or more petals, one or more expandable members, or a combination thereof together so that the sheath is formed. The one or more movable collars may form a friction fit with the core wire so that during installation the one or more movable collars move with the sheath and upon a retraction of the core wire, the moveable collar slips so that the ARD may be deployed. The one or more collars may be made of the same material as the sheath, the core wire, or both. The one or more movable collars may be attached to the one or more fiber strands, one or more petals, one or more expandable members, or a combination thereof by adhesion bonding, wire wrapping, or the like or any combination thereof. One or more movable collars may connect one or both ends of the one or more fiber strands, one or more petals, one or more expandable members, or a combination thereof so that each end may be twisted, one end may be twisted, or a combination of both. The one or more collars may be made of a plastic, a polymer, an elastomeric, metal, a natural material, a synthetic material, or a combination thereof.

Other physical characteristics of an ARD tending to cause a device to mechanically deform or actuate are also possible. For example, some materials exhibit piezo-electric characteristics that tend to cause the material to deform when the material is exposed to an electrical charge. In some embodiments, temperature changes can also cause a device to radially (and circumferentially) expand from an insertion state to a deployed state.

Grip tubes may be provided at the proximal end of the device that would be connected to both the outer sheath and the core wire to provide a gripping surface for rotating the core wire to launch the ARD. The grip tube may be attached to the core wire and would extend beyond the grip tube attached to the sheath, such that a user would be able to grasp and hold the grip tube attached to the sheath and rotate the grip tube attached to the core wire to deploy the ARD. The grip tube may be any device that a user may grip so that the sheath, the core wire, or both may be rotated. The grip tube may assist a user in twisting the core wire, the sheath, or both. The grip tube may be any device used to launch the ARD.

Various material compositions or forms, e.g., metal, plastic, polymer tube, fiber glass, and natural or synthetic fiber (strand or woven), may be suitable. A polymer, thin-wailed tube, or a fabric material, may be suitable for some embodiments (e.g., a tubular structure having oblique slits). A polymer that is less prone to damage by an applied laser energy in relevant spectrum may be suitable. ARDs as disclosed herein can be deployed by inducing a relative movement between a core member (e.g., a guide-wire) and a portion of the expandable portion of the ARD. In some instances, a proximal end of the expandable portion can be urged in a distal direction, or a distal end of the expandable portion can be urged in a proximal direction, as by withdrawing the core member. During a surgical procedure for removing debris from a body lumen, a safety guidewire can be placed in the lumen (e.g., ureter, via a uretero tube). The ARD can be positioned in the lumen using a technique similar to inserting a conventional guidewire. The ARD can have a hydrophilic, flexible tip sized to be able to pass between the debris and a nearby lumen wall.

The expandable portion of the ARD can be positioned distally relative to the debris by a selected distance. Subsequent to being positioned distally of the debris, the expandable portion of the ARD can be expanded as described above. The radially expanded ARD can occupy a sufficient volume and cross-sectional area of the lumen to prevent or substantially reduce the degree to which the debris can move in a retrograde direction during treatment or manipulation by the surgeon. In some instances, such as those concerning the removal of ureteral stones, ARDs as disclosed herein can be used to reduce or prevent retrograde movement of individual debris particles arising from breaking stones having a characteristic length (e.g., a cross-sectional dimension) of about 5 mm or larger. Typically, stones smaller than about 4 mm can be passed spontaneously without requiring ureteral lithotripsy. Typically, ureteral stones rarely have a characteristic length exceeding about 10 mm. The expandable portions, the sheath, the core wire, or a combination thereof may include one or more surface markings.

The surface marking may be any marking on the ARD that assists a user in deploying, retracting, inserting, or a combination thereof the device. The surface markings may indicate the amount of circumferential opening of the expandable portions that has occurred, the length of core wire that has been removed, the amount of twisting of the core wire, the amount of twisting of the sheath, or a combination thereof. The surface markings may be one or a series of marks that indicate the position of the ARD, the state of the ARD, or both.

The ARD of the teachings herein may be transformed into a configuration characterized as being three-dimensional (3-D), as shown in FIG. 2, for example. Such a 1-D (see FIG. 1) to a 3-D (see FIG. 2) transformation can be accomplished by shortening a distance between opposed ends of the tubular structure, as described more fully below and shown by way of example in FIG. 9A-9K.

Some innovative ARDs can have a physical configuration in a deployed state that wholly or partially forms a temporary, removable barrier behind (e.g., distally positioned relative to) a body of debris (e.g., a stone) in a body lumen. As shown in FIG. 1, the ARD 10 and the expandable portion 20 of the sheath may have a slim elongate configuration suitable to pass through a gap between a stone (not shown) and surrounding anatomy (e.g., a lumen wall, not shown). The expandable portion 20 can be positioned behind (distally of) the debris and can transform from the insertion state 100, as shown in FIG. 1, to a deployed state 110, as shown in FIG. 2, as by urging the distal collar 12 and the proximal collar 13 of the expandable portion 20 toward each other along the core wire 11 (e.g., through mechanical-, pneumatic-, chemical, or temperature-induced loading).

As is illustrated in FIGS. 1 and 3 a sheath 14 includes a non-expandable portion 21 proximate to the proximal end region 28 and distal end region 26. The sheath 14 includes an expandable portion 20 having a proximal (to the user) end region 28 that is affixed to the proximal collar 13, and the distal end region 26 of the expandable portion 20 that can be connected to a core wire 11 via a distal collar 12 in the distal end region 26. An intermediate region 30 is located between the distal end region 26 and the proximal end region 28. The proximal collar 12 and/or the distal collar 13 can move longitudinally along the longitudinal axis 112. The device shown in FIGS. 1 and 3 can change its configuration when the structure is compressed along the longitudinal axis 112 (e.g., when the core wire 11 is drawn through the sheath 14), causing expandable members 22 of the structure to buckle and expand radially outward, forming "petals" 34 (see FIG. 2) from the buckled members positioned between circumferentially adjacent slits 32.

As shown in FIG. 3, the sheath 14 has an expandable portion 20 and a non-expandable portion 21 configured to overlie a core, e.g., a guidewire 11 (as is shown in FIG. 1). The guidewire 11 can extend longitudinally through a hollow interior region 16 of the sheath 14. The sheath 14 extends between a distal end region 26 and a proximal end region 28. The expandable portion 20 is comprised of one or more expandable segments 24 (i.e., five) that are positioned between the distal end region 26 and the proximal end region 28 of the expandable portion 20. The longitudinally adjacent expandable segments 24 can be longitudinally spaced from each other by respective intermediate collars 18.

In FIG. 3, the sheath 14 longitudinally alternates between contiguous (e.g., not expandable in a radial direction) collars 18 and slit walls defining separate expandable members 22 configured to expand in a radial direction upon buckling under a longitudinally compressive load applied to the sheath 14. Such longitudinal spacing between expandable segments 24 can be beneficial but is not essential.

As illustrated in FIG. 5 and shown in the sequence of images shown in FIG. 9, urging the distal collar 12 and the proximal collar 13 (FIGS. 5 and 6) toward each other can urge the respective distal end region 26 and proximal end region 28 of the expandable portion 20 toward toward each other, placing the expandable portion 20, and each of the corresponding expandable segments 24 in compression. When a sufficient compressive load is applied to the expandable portion 20, at least one of the expandable members 22 in one of the expandable segments 24 will buckle. The sequence of images in FIGS. 10A-10K shows several intermediate states of buckling of the expandable segments 24. Although the expandable member 22 may buckle inwardly at the onset of buckling (e.g., under a critical buckling load), the guidewire 11 (or other member positioned in the hollow interior region 16) will tend to limit the extent of inward buckling, causing the expandable member to eventually buckle, and expand, radially outwardly.

As a given expandable member 22 buckles, the member's resistance to the compressive load substantially drops, transferring excess compressive loading to adjacent expandable members 22. As a critical buckling load is applied to each expandable member, the respective expandable member will buckle (eventually in a radially outward direction as just described), transforming the geometric configuration of the respective expandable segments 24 from a 1-D, insertion state as shown in FIGS. 1 and 3 to a 3-D, deployed state as shown in FIGS. 2, 4A-4B and 5.

The distal end region 26 is positioned adjacent a distal collar 12 and the proximal end 28 is positioned adjacent a proximal collar 13. The distal collar 12 is immovable relative to (e.g., affixed to) the guidewire 11, and the proximal collar 13 can be longitudinally movable relative to the guidewire. In other embodiments, the distal collar can be longitudinally movable relative to the guidewire 11, and the proximal collar 13 can be immovable relative to the guidewire.

The components shown in, for example, FIGS. 1 through 9A-9K and 10A1-10D3, have a number of longitudinally spaced, expandable segments. The pattern of circumferential separation of the members (e.g., partly helical apertures between adjacent members) is such that a proximal end of a given helical slit is circumferentially offset from an adjacent distal end of another helical slit by a selected circumferential angle (e.g., from one segment to the next segment). Each of the distal collar 12, the proximal collar 13 and the intermediate collars 18 are separate and distinct components from each other and the expandable segments 24. Alternatively, one or more of the distal collar 12, the proximal collar 13, and the intermediate collars 18 form a unitary construction with the expandable segments 24. FIG. 3 illustrates one example of an expandable portion 20 having a unitary construction with juxtaposed expandable segments 24 spaced from each other by respective intermediate collars 18.

Each expandable segment 24 shown in FIG. 3 defines a respective plurality of oblique slits 32 extending between a segment proximal end region 56 and a segment distal end region 54 of the respective expandable segments 24. Each slit 32 extends at an oblique angle relative to a longitudinal axis 112 of the hollow interior 16. Each oblique slit 32 partially defines a helically shaped aperture extending through the annular wall of the expandable portion 20. An expandable member 22 is defined between adjacent slits 32.

Figure 4B:
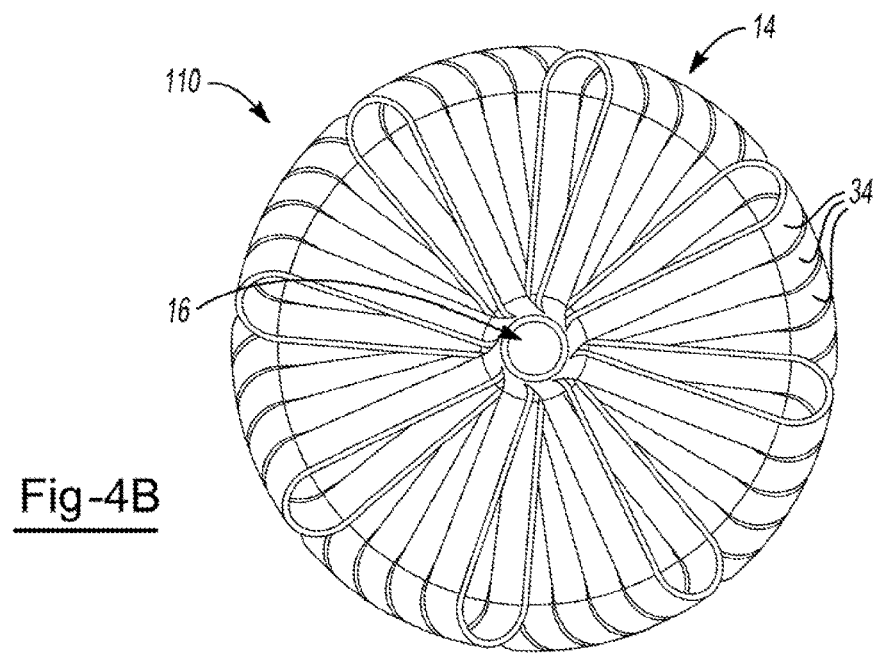

FIG. 4A shows a perspective view of expandable portion 20 in a deployed state 110. Each expandable segment 24 defines a plurality of circumferentially spaced expandable members 22 forming petals 34. Each petal 34 includes an upper petal portion 36 and a lower petal portion 38, which are twisted relative to each other as shown by arrows 114. FIG. 4B illustrates a top view of FIG. 4A. The hollow interior region 16 is shown extending through the sheath 14, and the petals 34 fill the circumference so that there are no longitudinal gaps through the sheath 14.

Figure 9H:
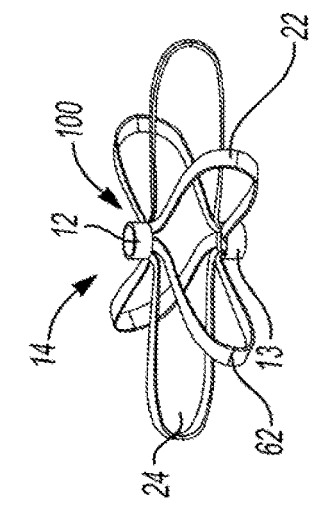
Figure 9I:
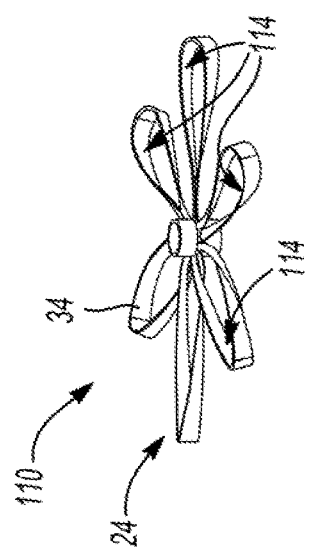
Figure 9J:
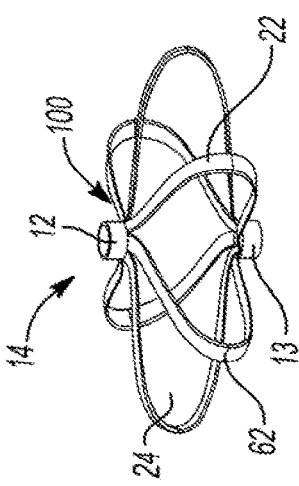
Figure 9K:
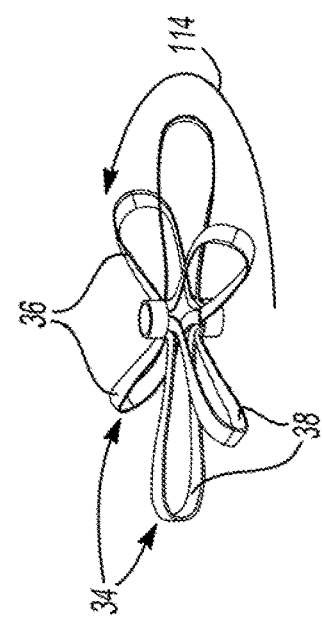

The twist 114 of the petals 34 in a single expandable segment 24 is further illustrated between FIG. 9J to FIG. 9K, an expandable member 22 twists and expands circumferentially to form a "petal" 34 so that each respective upper petal portion 36 and lower petal portion 38 are circumferentially offset from each other.

FIGS. 5 and 6 illustrate the ARD 2 during a change from an insertion state 100 (see FIG. 6) to a deployed state 110 (see FIG. 5). Once the ARD 2 is fully inserted through a gap (not shown) using the insertion cone 60 the core wire 11 is retracted and the proximal collar 13 is moved towards the distal collar 12 of the insertion cone 60. The core wire 11 is twisted so that the petals 34 twist.

Figure 7:
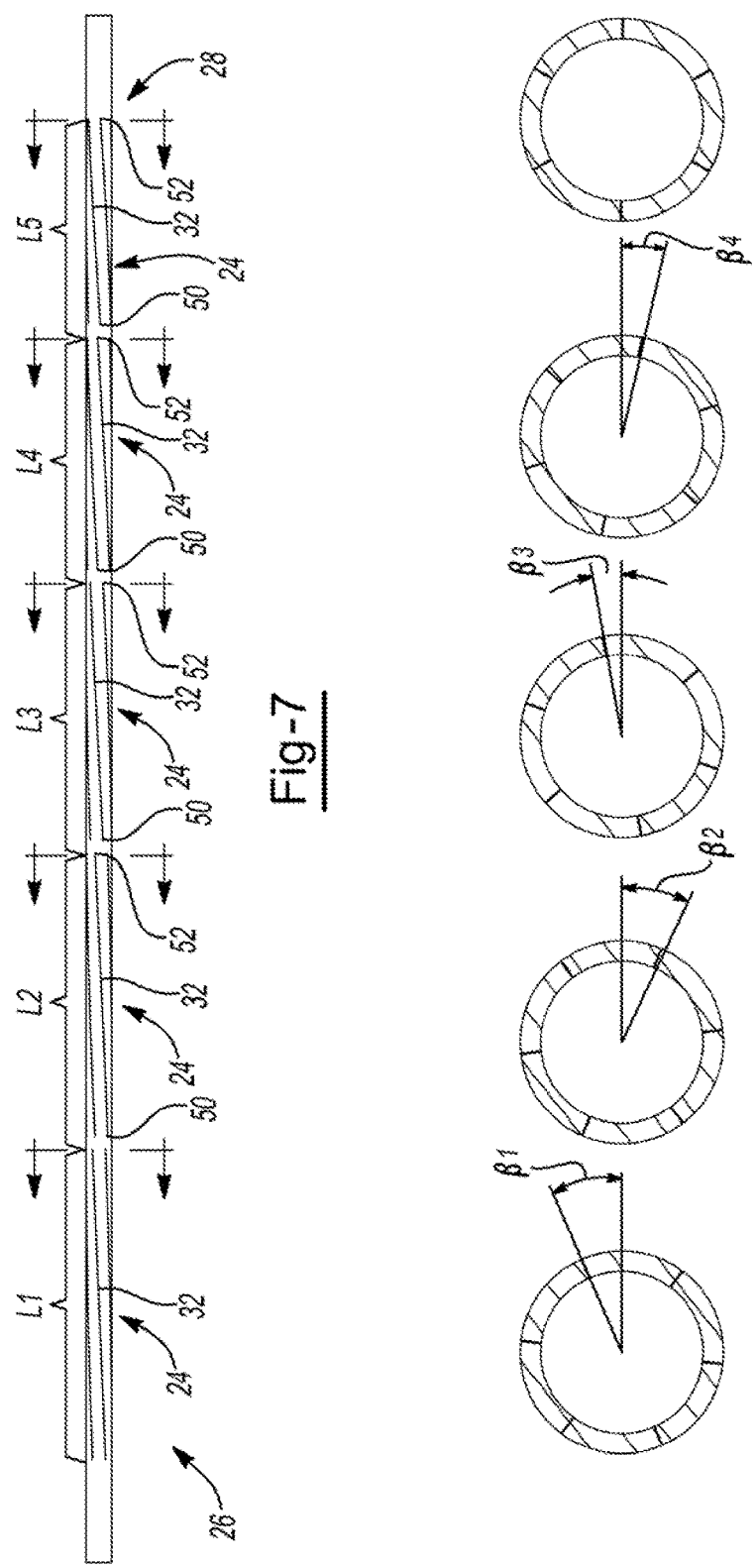
FIG. 7 illustrates several details of an embodiment of a sheath of an ARD.

FIGS. 7 and, 8 illustrate several details of innovative ARDs. FIGS. 10 through 1 illustrate examples of such devices in a deployed state. In FIG. 7, the expandable portion has five longitudinally spaced expandable segments 24, with each segment defining six oblique slits circumferentially spaced from each other by about 60°. The proximal end 52 and the distal end 50 of each adjacent oblique slit 32 are circumferentially offset from each other by about 60°, although other circumferential offsets are possible. For example, a circumferential offset between the distal end and the proximal end of a given oblique slit can range between about 0° and about 180°, such as between about 40° and about 90°, with some embodiments having an offset measuring between about 60° and about 72°. Each of the expandable segments 24 of FIG. 7 have a different length such that the lengths (L1, L2, L3, L4, and L5) each decrease from the distal end region 26 to the proximal end region 28. The proximal end of an oblique slit can be circumferentially offset from the distal end of a longitudinally adjacent oblique slit. As illustrated the circumferential offset varies from β1 to β2 to β3 and to β4 from the distal end region 26 to proximal end region 28 as the slits 32 of each respective expandable segment 24 are varied. In some instances, the offset (β) between longitudinally spaced oblique slits can range between about 0° and about ½ of the circumferential spacing between adjacent slits in a given expandable segment. For example, in FIG. 7, adjacent slits are circumferentially spaced from each other by about 60°. In this example, longitudinally spaced slits can be circumferentially offset from each other by between about 0° and about 30°

Each of the expandable segments 24 of FIG. 8 are the same length (L). Further, the circumferential offset between a proximal end 52 and a distal end 50 of two adjacent slits 32 is less when compared to FIG. 7. Thus, β1' has the same angle and same offset above the longitudinal axis and β2' is offset below the axis so that when deployed the ARD fills a body lumen.

FIG. 9A through 9K illustrates a sequence of transformation of one expandable segment 24 from an insertion state 100 to a fully deployed state 110. As shown in FIG. 9A, the sheath 14 includes a distal collar 12 and a proximal collar 13 with a plurality of expandable members 22 therebetween that represent one expandable segment 24. Each expandable member 22 includes a buckling feature 62 so that each expandable member 22 buckles at a predetermined location. FIGS. 9H through 9I demonstrate the transformation of each segment from a plurality of expandable member 22 to a plurality of petals 34. In FIG. 9J when the expandable member 22 is buckled and formed into a petal 34 the upper petal portion 36 is twisted in the direction 114 relative to the lower petal portion 38.

FIGS. 10A1-10D3 illustrate a number of alternative configurations of expandable segments 24 in a deployed (expanded) state. In FIG. 10, each row of images depicts a selected number and relative configuration of expandable segments. For example, each in the first row of images A1, B1, C1, D1 depicts an expandable portion 20 having a single expandable segment 24.

Each in the second row of images A2, B2, C2, D2 depicts an expandable portion 20 having five longitudinally spaced expandable segments 24. Each expandable segment 24 has a unique length. An expandable portion 20 of an ARD having a plurality of different-length expandable segments can allow for a more controlled expansion of the expandable portion. For example, a longer expandable segment will typically buckle (e.g., expand) under a lower compressive load relative to the load under which a shorter expandable segment will buckle. Accordingly, as compressive loading of an expandable portion of an ARD increases, the respectively different-length segments will tend to expand sequentially from longer segments to shorter segments. In one embodiment, the expandable segments 24 successively increase in length from the distal (shortest) expandable segment 24 to the proximal (longest) expandable segment. As each end-elevation view (from a distal position looking toward the distal end of the respective radially expanded ARDS) of FIGS. 10A2, 10B2, 10C2 and 10D2 depict, the resulting configuration of the ARD in the deployed state can be somewhat cone-like.

A sequence of buckling among a plurality of expandable segments can be controlled using other approaches. For example, a portion of one or more expandable members 22 in each respective expandable segment 24 can be removed to reduce a corresponding critical buckling load of each of the one or more expandable members. Under such an approach, relatively more material can be removed from each successive expandable segment (e.g., to form a narrow "waist" in each segment) according to a selected buckling sequence, with the segments having more material removed typically buckling under relatively lower compressive loads.

Approaches for controlling a sequence of buckling among a plurality of expandable segments can be combined. For example, each expandable segment can have a corresponding length different from a length of one or more other expandable segments, and material can be removed from one or more expandable members corresponding to a given expandable segment to define a waist.

Each in the third column of images A3, B3, C3, D3 depict a respective expandable portion having five expandable segments of substantially identical length.

Each row (e.g., A1, B1, C1, D1) of images in FIG. 10 depicts expandable portions having a selected number and configuration of oblique slits (and a corresponding number and configuration of expandable members between adjacent oblique slits). Each expandable segment in Row A (i.e., images A1, A2, A3) has six oblique slits equally spaced from each other circumferentially (i.e., spaced from each other at 60°). As well, each respective distal end corresponding to each oblique slit in Column A is circumferentially offset from the corresponding proximal end by 60°.

Each expandable segment in Row B (i.e., images B1, B2, B3) has six oblique slits equally spaced from each other circumferentially (i.e., spaced from each other at 60°). As well, each respective distal end corresponding to each oblique slit in Row B is circumferentially offset from the corresponding proximal end by 120°.

Each expandable segment in Row C (i.e., images C1, C2, C3) has five oblique slits equally spaced from each other circumferentially (i.e., spaced from each other at 72°). As well, each respective distal end corresponding to each oblique slit in Row C is circumferentially offset from the corresponding proximal end by 72°.

Each expandable segment in Row D (i.e., images D1, D2, D3) has six oblique slits equally spaced from each other circumferentially (i.e., spaced from each other at 60°). As well, each respective distal end corresponding to each oblique slit in Row D is circumferentially offset from the corresponding proximal end by 72°. The expandable portion of the ARD shown in Row D is configured as a sheath that can overlie a sheathed guidewire (e.g., a guidewire having a sheath member positioned between the expandable ARD and the guidewire). For example, in the insertion state, the expandable portion shown in Row D has an outer diameter of about 5.1 Fr.

In contrast, the embodiments shown in Rows A, B and C are configured as respective guidewire sheaths. For example, the embodiments shown in Rows A, B and C have an outer diameter of about 3 Fr., and are configured to directly overlie a guidewire (e.g., without a sheath positioned between the expandable portion of the ARD and the guidewire).

Figure 11:
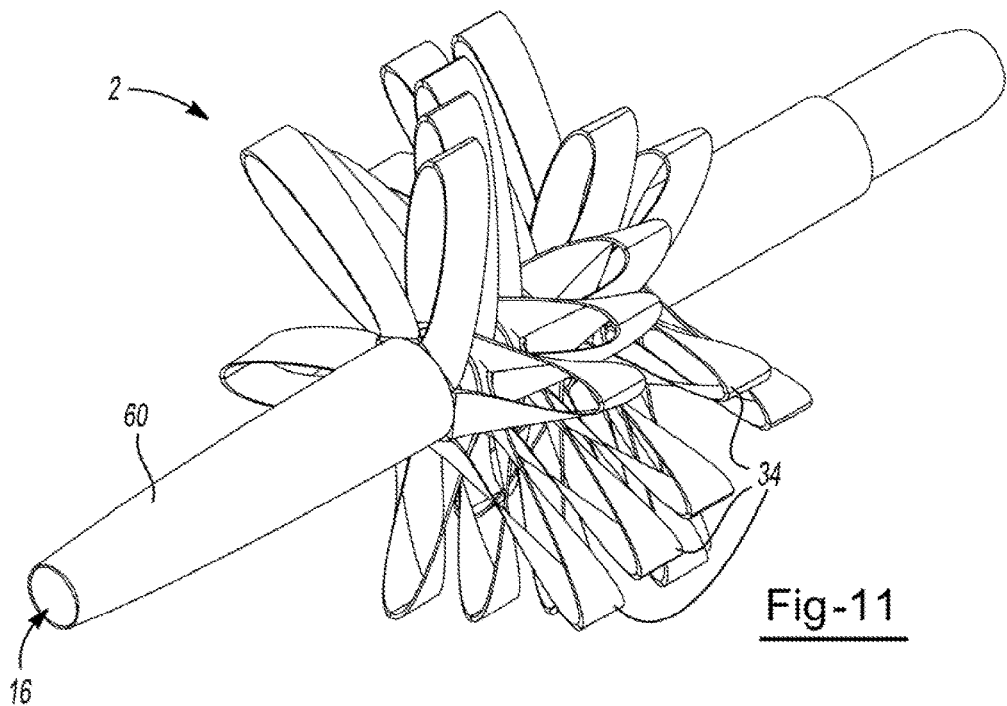
FIG. 11 illustrates an alternative embodiment of an ARD configured to overlie a guidewire.

FIG. 11 illustrates an ARD 2 having an insertion cone 60 with a hollow interior region 16 so that the ARD 2 can be located on a guidewire (not shown) and the guidewire can extend through the ARD 2. As illustrated, each of the petals 34 has substantially the same length.

Figure 12:
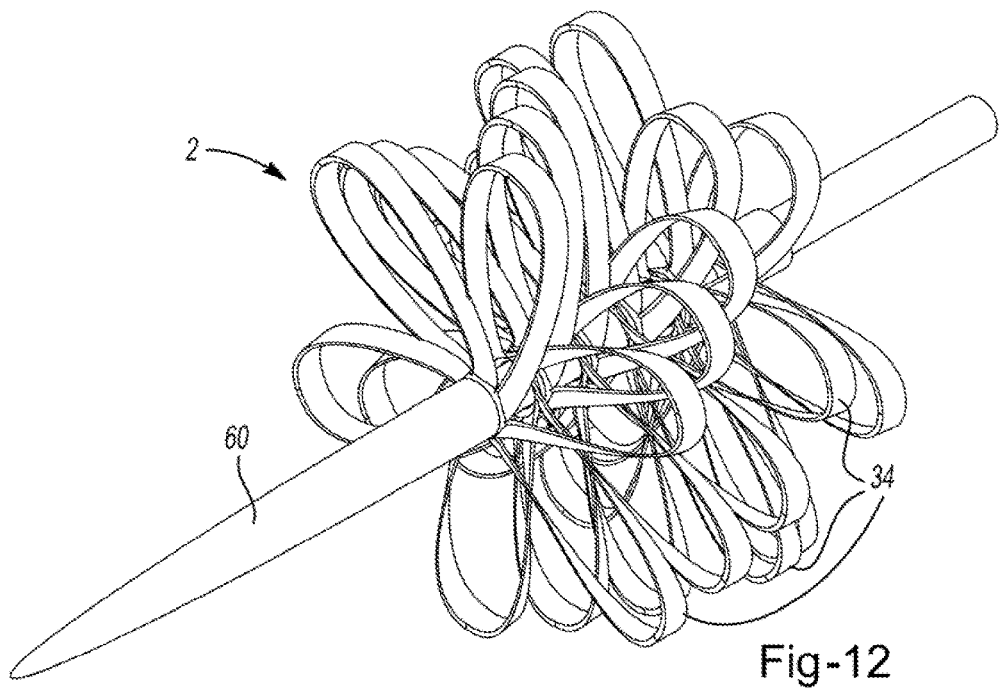
FIG. 12 illustrates another alternative embodiment of an ARD having several expandable segments with differing lengths, forming a "cone-shaped" ARD in a deployed state.
Figure 13:
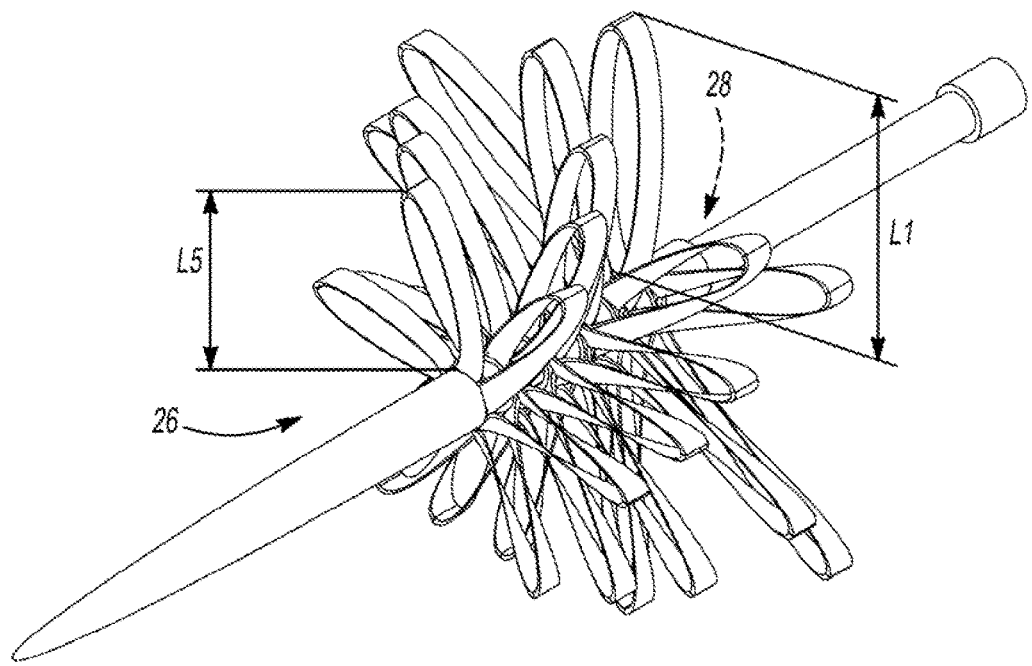
FIG. 13 illustrates another alternative embodiment of an ARD having several expandable segments with differing lengths.

FIGS. 12 and 13 show representative isometric views of expandable portions of ARDs having a variation in length of the expandable segments. The petals 34 of FIG. 13 have a length L1 at a proximal end region 28 that is longer than the petals at the distal end region 26 having a length L5.

Figure 14:
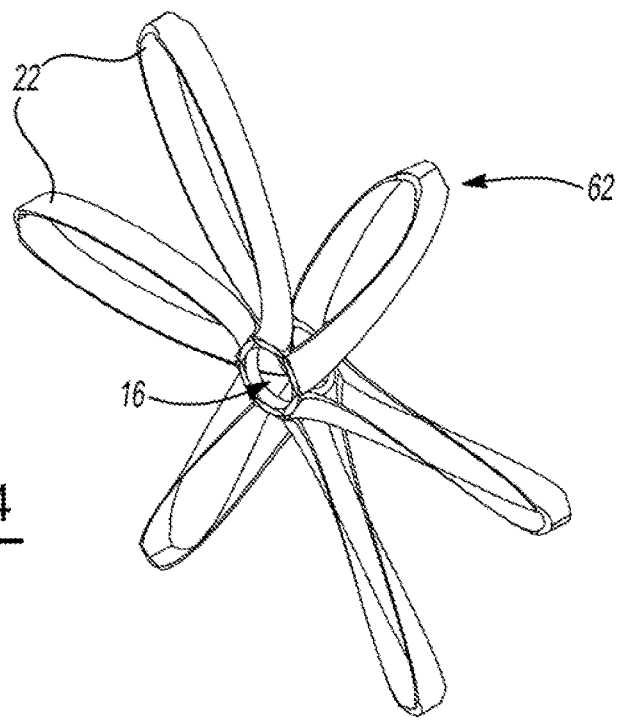
FIG. 14 illustrates an alternative embodiment of an ARD having several expandable segments with material removed from one or more expandable members to promote buckling of the respective one or more expandable members (and/or the corresponding expandable segments) in a selected order.

FIG. 14 illustrates one expandable segment 24 having a hollow interior region 16 and expandable members 22 including one possible example of a buckling feature 62. The buckling feature 62 as illustrated has material removed from the edges of each expandable member 22.

Figure 15:
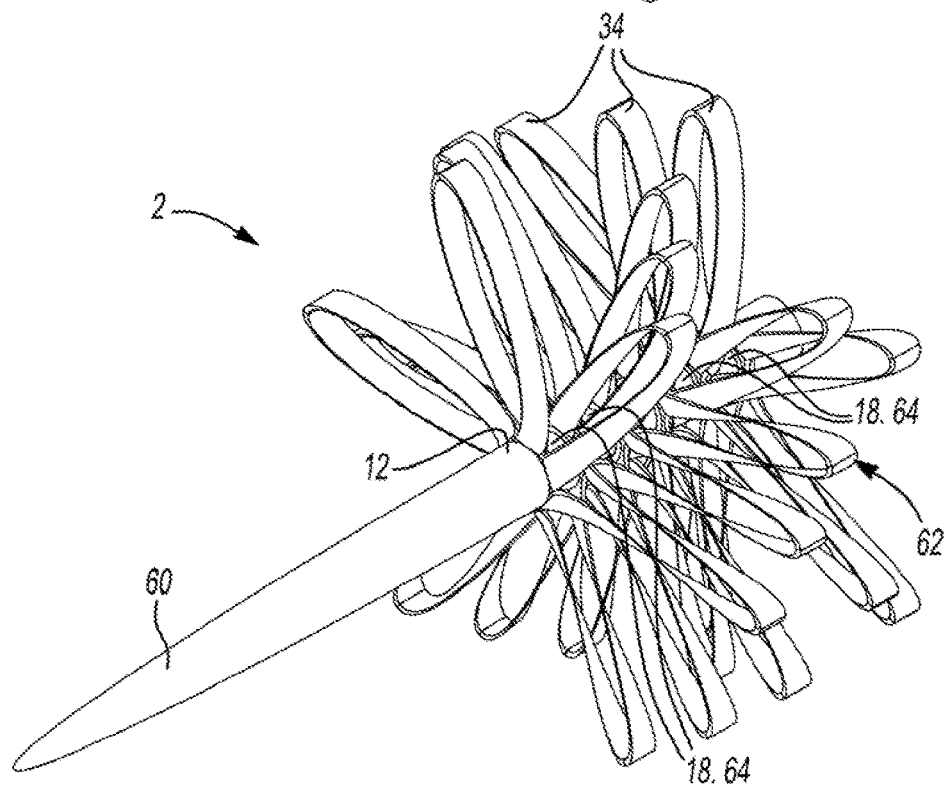
FIG. 15 illustrates another alternative embodiment of an ARD having several expandable segments with material removed from one or more expandable members.

FIG. 15 illustrates an example of an ARD 2 including a narrow waste region 64 formed by an intermediate collar 18 being between each petal 34. As illustrated, the insertion cone 60 acts as the distal collar 12.

FIGS. 16 through 17 illustrate an alternative embodiment of an expandable portion 20 of a sheath 14. As shown in FIG. 16 the ARD 2 is in the insertion state 100. The expandable portion 20 has a plurality of fiber strands 41 extending between a proximal collar 13 and a distal collar 12. The proximal end of each respective fiber can be fixedly coupled to the proximal collar 13, and the distal end of each respective fiber can be fixedly coupled to the distal collar 12. The distal collar 12 can be fixedly coupled to the guidewire 11. The proximal collar 13 can be longitudinally moveable relative to the guidewire 11 such that the proximal collar 13 and the distal collar 12 can be urged toward and apart from each other. As shown in FIG. 17, drawing the proximal collar 13 toward the distal collar 12 can cause the plurality of fiber strands 41 to buckle and expand radially outwardly. Although the fibers are shown as being discretely and orderly buckled in FIG. 17 to form a deployed state 110, as a result of limitations of the software used to develop and render a three-dimensional model of the expandable portion 20, it is anticipated that the fiber strands 41 are likely to buckle in a somewhat less orderly manner, and possibly become intertwined with each other when radially expanded.

In FIGS. 16 and 17, the plurality of fiber strands 41 have an outer diameter of about 1 mm. In one contemplated embodiment, 72 individual fibers are arranged in two concentric rings of fibers (i.e., one ring of fibers concentrically positioned relative to the other ring of fibers). The pair of concentric rings of fibers can define a wall thickness of about 0.1 mm. In other contemplated embodiments, several (e.g., more than about 10 and fewer than about 100) fibers can be arranged to form an annular ring of fibers. A thickness of the ring (e.g., a "wall" thickness) can measure less than 1 mm, e.g., less than about 0.5 mm, with about 0.1 mm being but one example.

Figure 18:
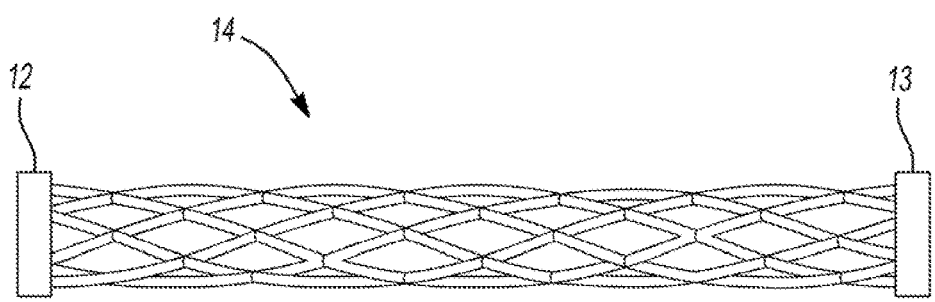
FIG. 18 illustrates an alternative embodiment of an ARD with an expandable segment having a mesh configuration.

With suitable materials (e.g., combining a suitable amount of flexibility and column strength), a mesh configuration can also transform from a "long and slim" configuration to a "wide and short" configuration. FIG. 18 shows such an embodiment.

With a mesh structure as shown in FIG. 18, with a distal collar 12 and a proximate collar 13 with sheath 14 there between forming a middle section. The expansion of the middle section (e.g., when the opposed ends are urged together) is generally more constrained and limited compared to the device shown in FIGS. 5, 6 and 7, above. Nonetheless, even with a very soft, pliable material, a mesh structure can reduce a likelihood of tangling between expanded members. With the principles disclosed herein, it is possible to design, construct and use a wide variety of apparatus configured to reduce or eliminate retropulsion of a body or other debris within a body lumen during a surgical procedure.

This disclosure makes reference to the accompanying drawings which form a part hereof, wherein like numerals designate like parts throughout. The drawings illustrate specific embodiments, but other embodiments may be formed and structural changes may be made without departing from the intended scope of this disclosure. Directions and references (e.g., up, down, top, bottom, left, right, rearward, forward, etc.) may be used to facilitate discussion of the drawings but are not intended to be limiting. For example, certain terms may be used such as "up," "down,", "upper," "lower," "horizontal," "vertical," "left," "right," and the like. These terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" surface can become a "lower" surface simply by turning the object over. Nevertheless, it is still the same surface and the object remains the same. As used herein, "and/or" means "and" as well as "and" and "or."

Accordingly, this detailed description shall not be construed in a limiting sense, and following a review of this disclosure, those of ordinary skill in the art will appreciate the wide variety of imaging systems that can be devised and constructed using the various concepts described herein. Moreover, those of ordinary skill in the art will appreciate that the exemplary embodiments disclosed herein can be adapted to various configurations without departing from the disclosed concepts. Thus, in view of the many possible embodiments to which the disclosed principles can be applied, it should be recognized that the above-described embodiments are only examples and should not be taken as limiting in scope. I therefore reserve the right claim as my inventions a that come within the scope and spirit of this disclosure.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc, are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and ail numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

I currently claim:

1. A method comprising:
   positioning an anti-retropulsion device at a desired location; and
   expanding an expandable portion of the anti-retropulsion device, the expandable portion comprises plurality of expandable segments that extend along a longitudinal axis, and each of the plurality of expandable segments have a corresponding plurality of expandable members; and
   wherein after the expanding, the expandable members in one of the expandable segments are circumferentially offset relative to the expandable members in another one of the expandable segments such that formation of longitudinally extending gaps between the expandable members, and extending along an entire longitudinal length of the expandable members, is prevented.

2. The method of claim 1, wherein the method includes:
   moving a core wire so that a distance between a distal collar and a proximal collar is reduced and the expandable portion is expanded; and
   rotating the core wire at an angle so that the expandable portion twists.

3. The method of claim 1, wherein the method includes a step of inserting the anti-retropulsion device into a lumen and pushing the anti-retropulsion device through the lumen so that the anti-retropulsion device is located at the desired location.

4. The method of claim 1, wherein the method includes a step of sliding the anti-retropulsion device over a core wire and pushing the core wire until the anti-retropulsion device is located at the desired location.

5. The method of claim 2, wherein the method includes a step of removing the anti-retropulsion device from the desired location while the anti-retropulsion device is expanded.

6. The method of claim 2, wherein the method includes a step of returning the expandable portion to an unexpanded state and removing the anti-retropulsion device from the desired location.

7. The method of claim 3, wherein when the expandable portion is expanded, the expandable members are expanded in the lumen so that formation of the longitudinally extending gaps between the expandable members is prevented and debris are prevented from moving in the lumen past the expandable members.

8. The method of claim 7, wherein the expandable members in one of the expandable segments are circumferentially offset relative to the expandable members in an adjacent expandable segment.

9. The method of claim 1, wherein during the expanding step, the expandable members expand and form petals,
wherein each petal includes an upper petal portion and a lower petal portion, and the upper petal portion is twisted relative to the lower petal portion.

10. The method of claim 7, wherein the anti-retropulsion device comprises:
a distal collar that is positioned distally of the plurality of expandable segments, and a proximal collar that is positioned proximally of the plurality of expandable segments,
wherein during the expanding step, the expandable members expand or contract radially and circumferentially in correspondence with a change in spacing between the distal collar and the proximal collar, and
wherein before the expanding step, the method includes a step of inserting the anti-retropulsion device into a body lumen so that debris are prevented from moving in the body lumen past the expandable members after the expanding step.

11. The method of claim 10, wherein the expandable members are sufficiently elastic so that when the expandable members are expanded in the body lumen, the expandable members contact the body lumen and at least partially deform.

12. The method of claim 1, wherein the anti-retropulsion device comprises:
an elongate tubular sleeve extending along a longitudinal axis defining an outer wall having:
a proximal wall portion defining a first plurality of apertures, each of the first plurality of apertures having:
a proximal end, and
a distal end;
a distal wall portion longitudinally spaced from the proximal wall portion, the distal wall portion defining a second plurality of apertures having:
a proximal end,
a distal end; and
an intermediate wall portion located between the proximal wall portion and the distal wall portion;
wherein the proximal end and the distal end of each of the first plurality of apertures, the second plurality of apertures, or both are positionally offset in an ordinate direction;
wherein each of the proximal ends of the second plurality of apertures are offset in an ordinate direction from each of the distal ends of the first plurality of apertures; and
wherein the method includes a step of urging a distal end of the elongate tubular sleeve toward a proximal end of the elongate tubular sleeve so that one or more of the expandable members defined by adjacent first apertures and adjacent second apertures are expanded, and
before the expanding step, the method includes a step of inserting the anti-retropulsion device into a body lumen so that when the expandable members are expanded, formation of longitudinally extending gaps in the body lumen is prevented.

13. A method comprising:
inserting an anti-retropulsion device into a body lumen, the anti-retropulsion device includes an expandable portion comprising a plurality of expandable segments extending along a longitudinal axis, and each of the expandable segments comprises a plurality of expandable members, and
expanding the expandable portion so that the expandable members in an adjacent one of the expandable segments are circumferentially offset relative to the expandable members in another one of the expandable segments such that formation of longitudinally extending gaps between the expandable members and extending along an entire longitudinal length of the plurality of the expandable segments is prevented so that debris are prevented from moving in the body lumen past the expandable members, and
wherein the expandable members are sufficiently elastic so that during the expanding, the expandable members contact the body lumen and at least partially deform.

14. The method of claim 13, wherein the expanding step comprises moving a core wire so that a distance between a distal collar and a proximal collar is reduced,
wherein the expandable members expand or contract radially and circumferentially in correspondence with a change in spacing between the distal collar and the proximal collar.

15. The method of claim 13, wherein the anti-retropulsion device comprises a sheath having a generally annular cross-section,
wherein each of the expandable members is defined between a pair of oblique slits extending through the sheath.

16. The method of claim 14, wherein after the moving step, the method includes a step of twisting the anti-retropulsion device so that angles are formed between adjacent expandable members.

17. The method of claim 13, wherein during the expanding step, the plurality of expandable members expand and form petals,
wherein each petal includes an upper petal portion and a lower petal portion, and the upper petal portion is twisted relative to the lower petal portion.

18. The method of claim 13, wherein the expandable members in the one of the expandable segments relative to the expandable members in the another one of the expandable segments are circumferentially offset by an angle between 5 degrees and 30 degrees.

19. The method of claim 13, wherein two or more of the expandable segments have a different length.

20. A method comprising:
positioning an anti-retropulsion device at a desired location;
expanding an expandable portion of the anti-retropulsion device, the expandable portion comprises a plurality of expandable segments extending along a longitudinal axis, and each of the plurality of expandable segments have a corresponding plurality of expandable members;

changing a spacing between a distal collar and a proximal collar during the expanding step so that the expandable members are expanded or contracted radially and circumferentially, the distal collar is positioned distally of the plurality of expandable segments, and the proximal collar is positioned proximally of the plurality of expandable segments; and twisting the anti-retropulsion device so that angles are formed between adjacent expandable members;

wherein the expandable members are sufficiently elastic so that during the expanding step, the expandable members contact the body lumen and at least partially deform;

wherein during the expanding step, the plurality of expandable members form petals, and each of the petals includes an upper petal portion and a lower petal portion, and the upper petal portion is twisted relative to the lower petal portion; and wherein before the expanding step, the method comprises a step of inserting the anti-retropulsion device into a body lumen so that when the expandable members are expanded, the expandable members in one of the expandable segments are circumferentially offset relative to the expandable members in another one of the expandable segments such that formation of longitudinally extending gaps between the expandable members, and extending along an entire longitudinal length of the expandable members, is prevented so that debris are prevented from moving in the body lumen past the expandable members.

* * * * *